United States Patent
Doheny et al.

(10) Patent No.: US 12,207,949 B2
(45) Date of Patent: Jan. 28, 2025

(54) NON-CONTACT DIAGNOSIS AND MONITORING OF SLEEP DISORDERS

(71) Applicants: ResMed Pty Ltd, Bella Vista (AU); ResMed Sensor Technologies Limited, Clonskeagh (IE)

(72) Inventors: Emer Doheny, Clonskeagh (IE); Luke Gahan, Clonskeah (IE); Rami Khushaba, Sydney (AU); Emer O'Hare, Clonskeagh (IE); Alberto Zaffaroni, Clonskeagh (IE)

(73) Assignees: ResMed Pty Ltd (AU); ResMed Sensor Technologies Limited (IE)

( * ) Notice: Subject to any disclaimer, the term of this patent is extended or adjusted under 35 U.S.C. 154(b) by 978 days.

(21) Appl. No.: 15/778,511

(22) PCT Filed: Dec. 8, 2016

(86) PCT No.: PCT/EP2016/080267
§ 371 (c)(1),
(2) Date: May 23, 2018

(87) PCT Pub. No.: WO2017/097907
PCT Pub. Date: Jun. 15, 2017

(65) Prior Publication Data
US 2018/0353138 A1  Dec. 13, 2018

Related U.S. Application Data

(60) Provisional application No. 62/264,477, filed on Dec. 8, 2015.

(51) Int. Cl.
*A61B 5/00* (2006.01)
*A61B 5/05* (2021.01)
(Continued)

(52) U.S. Cl.
CPC .............. *A61B 5/7275* (2013.01); *A61B 5/05* (2013.01); *A61B 5/0507* (2013.01);
(Continued)

(58) Field of Classification Search
CPC ...... A61B 5/05–068; A61B 5/11–1101; A61B 5/1113; A61B 5/1114;
(Continued)

(56) References Cited

U.S. PATENT DOCUMENTS 4,197,537 A   4/1980  Follen et al.
5,361,070 A   11/1994 McEwan
(Continued)

FOREIGN PATENT DOCUMENTS

WO        2013152403 A1      10/2013
WO        WO-2013177621 A1 * 12/2013  ............... A61B 5/08

OTHER PUBLICATIONS

Zhou, Huiyu, et al. "Classification of upper limb motion trajectories using shape features." IEEE Transactions on Systems, Man, and Cybernetics, Part C (Applications and Reviews) 42.6 (2011): 970-982. (Year: 2011).*

(Continued)

*Primary Examiner* — Puya Agahi
*Assistant Examiner* — Jairo H Portillo
(74) *Attorney, Agent, or Firm* — Botos Churchill IP Law LLP

(57) ABSTRACT

A sensor may be configured to detect periodic limb movement in a sleeping person. The sensor may be a non-contact sensor, such as a radar motion sensor. The sensor may include a radio frequency transmitter for emitting radio frequency signals toward the person. The sensor may include a receiver for receiving reflected ones of the emitted radio frequency signals and processing the reflected ones of the emitted radio frequency signals to produce motion (Continued)

signal(s). A processor, such as one integrated with or coupled to the sensor, may evaluate the motion signals, such as in-phase and quadrature motion signals, and generate an indicator to identify occurrence of periodic limb movement in the motion signals based on the evaluation of the motion signals.

64 Claims, 15 Drawing Sheets

(51) Int. Cl.
    *A61B 5/0507*     (2021.01)
    *A61B 5/11*     (2006.01)
    *A61B 5/113*     (2006.01)

(52) U.S. Cl.
    CPC ........... *A61B 5/1101* (2013.01); *A61B 5/1113* (2013.01); *A61B 5/1121* (2013.01); *A61B 5/1126* (2013.01); *A61B 5/113* (2013.01); *A61B 5/4082* (2013.01); *A61B 5/4818* (2013.01); *A61B 5/7264* (2013.01); *A61B 5/4815* (2013.01); *A61B 5/6889* (2013.01); *A61B 5/6891* (2013.01); *A61B 2505/07* (2013.01); *A61B 2562/0228* (2013.01)

(58) Field of Classification Search
    CPC ....... A61B 5/1116–1118; A61B 5/1121; A61B 5/1122; A61B 5/1126–1128; A61B 5/4082–4094; A61B 5/4806–4818; A61B 5/7235–7278
    See application file for complete search history.

(56) References Cited

U.S. PATENT DOCUMENTS

| | | | |
|---|---|---|---|
| 5,682,164 A | 10/1997 | McEwan | |
| 5,966,090 A | 10/1999 | McEwan | |
| 6,426,716 B1 | 7/2002 | McEwan | |
| 7,616,988 B2 | 11/2009 | Stahmann et al. | |
| 7,887,493 B2 | 2/2011 | Stahmann | |
| 7,952,515 B2 | 5/2011 | McEwan | |
| 2004/0010202 A1* | 1/2004 | Nakatani | A61B 5/0816 600/529 |
| 2004/0267325 A1* | 12/2004 | Geheb | A61B 5/6833 607/5 |
| 2008/0009685 A1* | 1/2008 | Kim | A61B 5/4815 600/300 |
| 2009/0203972 A1* | 8/2009 | Heneghan | A61B 5/0816 600/301 |
| 2010/0152600 A1* | 6/2010 | Droitcour | A61B 5/1114 600/534 |
| 2010/0204550 A1 | 8/2010 | Heneghan et al. | |
| 2010/0214158 A1 | 8/2010 | McEwan | |
| 2010/0219955 A1* | 9/2010 | Demirdjian | G08B 21/06 340/575 |
| 2011/0301487 A1* | 12/2011 | Abeyratne | G16H 50/50 600/544 |
| 2012/0022348 A1* | 1/2012 | Droitcour | G01S 13/825 600/407 |
| 2013/0053653 A1* | 2/2013 | Cuddihy | G16H 50/30 600/301 |
| 2013/0131465 A1* | 5/2013 | Yamamoto | A61B 5/7271 600/300 |
| 2013/0261478 A1* | 10/2013 | Bonan | A61B 5/7203 600/516 |
| 2014/0024917 A1 | 1/2014 | McMahon et al. | |
| 2014/0046184 A1* | 2/2014 | Heinrich | A61B 8/00 600/595 |
| 2014/0136141 A1* | 5/2014 | Pan | A61B 5/1122 702/141 |
| 2014/0139616 A1* | 5/2014 | Pinter | A61B 5/742 348/14.08 |
| 2014/0163343 A1 | 6/2014 | Heneghan et al. | |
| 2014/0371547 A1* | 12/2014 | Gartenberg | A61B 5/0048 600/301 |
| 2015/0164375 A1* | 6/2015 | Schindhelm | G16H 50/20 600/534 |
| 2015/0216424 A1 | 8/2015 | McMahon et al. | |
| 2015/0374310 A1* | 12/2015 | Lee | A61B 5/7285 600/483 |
| 2016/0100766 A1* | 4/2016 | Yoshioka | A61B 5/7278 600/301 |
| 2016/0324446 A1* | 11/2016 | Prerau | A61B 5/0533 |
| 2017/0325717 A1* | 11/2017 | Dellimore | A61B 5/0823 |
| 2018/0049669 A1* | 2/2018 | Vu | A61B 5/0507 |

OTHER PUBLICATIONS

International Search Report mailed Mar. 17, 2017 to PCT Application No. PCT/EP2016/080267.
Restless Legs Syndrome Fact Sheet, National Institute of Neurological Disorders and Stroke, http://www.ninds.nih.gov/disorders/restless_legs/detail_restless_legs.htm, May 9, 2017.
Written Opinion mailed Mar. 17, 2017 to PCT Application No. PCT/EP2016/080267 filed December 8. 2016.
Stanford PLM automatic detector (S-PLMAD)—'Design and validation of a periodic leg movement detector.', Moore et al., PLoS One. 2014.
Hanly PJ, Zuberi-Khokhar N, Periodic limb movements during sleep in patients with congestive heart failure., Chest, 1996.
De Chazal, P., Fox, N., O'Hare, E., Heneghan, C., Zaffaroni, A., Boyle, P., . . . & McNicholas, W. T., 'Sleep/wake measurement using a non-contact biomotion sensor', Journal of sleep research, 2011.
Bhopi, et al., 'Can a Novel Smartphone Application Detect Periodic Limb Movements?' Global Telehealth, 2012.
Eği, et al., "Automatic Detection of Periodic Limb Movements in Sleep (PLMS) disorder by TMS320C6713 Digital Signal Processing Card", IEEE Signal Processing and Communications Applications Conference, 2010.

* cited by examiner

NON-CONTACT DIAGNOSIS AND MONITORING OF SLEEP DISORDERS

CROSS-REFERENCE TO RELATED APPLICATIONS

The present application is a national phase entry under 35 U.S.C. § 371 of International Application No. PCT/EP2016/080267 filed Dec. 8, 2016, published in English, which claims priority from U.S. Provisional Patent Application No. 62/264,477 filed Dec. 8, 2015, all of which are incorporated herein by reference.

STATEMENT REGARDING FEDERALLY SPONSORED RESEARCH OR DEVELOPMENT

Not Applicable

SEQUENCE LISTING

Not Applicable

FIELD OF THE TECHNOLOGY

The present technology relates to methods and apparatus for detection of characteristics of living subjects. More particularly, it relates to sensing or detecting periodic limb movements or other similar bodily movements with non-contact sensors such as radio frequency sensors or other monitoring apparatus.

BACKGROUND OF THE TECHNOLOGY (A) Monitoring Apparatus

Various non-contact sensors have been developed for movement detection. For example, continuous wave (CW) Doppler radar motion sensors emit a continuous wave radio frequency (RF) carrier and mix the transmitted RF with the return echoes to produce a difference frequency equal to the Doppler shift produced by a moving target. These sensors do not have a definite range limit (i.e., they can receive signals for both near and far objects, with the received signal being a function of radar cross section). This can lead to false triggers i.e., motion artefact interference. They may also have an undesirably high sensitivity at close range that leads to false triggering.

A pulse Doppler motion sensor is described in U.S. Pat. No. 4,197,537 to Follen et al. A short pulse is transmitted and its echo is self-mixed with the transmitted pulse. The pulse width defines the range-gated region. When the transmit pulse ends, mixing ends and target returns arriving after the end of the transmit pulse are not mixed and are thereby gated out.

A Differential pulse Doppler motion sensor disclosed in U.S. Pat. No. 5,966,090, "Differential Pulse Radar Motion Sensor," to McEwan, alternately transmits two pulse widths. It then subtracts the Doppler responses from each width to produce a range gated Doppler sensing region having a fairly constant response versus range.

Impulse radar, such as that described in U.S. Pat. No. 5,361,070, "Ultra-Wideband Radar Motion Sensor," to McEwan produces a very narrow sensing region that is related to the transmitted impulse width. A two-pulse Doppler radar motion sensor, as described in U.S. Pat. No. 5,682,164, "Pulse Homodyne Field Disturbance Sensor," to McEwan, transmits a first pulse and after a delay generates a second pulse that mixes with echoes from the first pulse. Thus a range gated sensing band is formed with defined minimum and maximum ranges. UWB radar motion sensors have the disadvantage of not having global RF regulatory acceptance as an intentional radiator. They also have difficulty sensing objects at medium ranges and in some embodiments can be prone to RF interference.

A modulated pulse Doppler sensor is described in U.S. Pat. No. 6,426,716 to McEwan. The range gated microwave motion sensor includes adjustable minimum and maximum detection ranges. The apparatus includes an RF oscillator with associated pulse generating and delay elements to produce the transmit and mixer pulses, a single transmit (TX)/receive (RX) antenna or a pair of separate TX and RX antennas, and an RF receiver, including a detector/mixer with associated filtering, amplifying and demodulating elements to produce a range gated Doppler signal from the mixer and echo pulses.

In U.S. Pat. No. 7,952,515, McEwan discloses a particular holographic radar. It adds a range gate to holographic radar to limit response to a specific downrange region. McEwan states that cleaner, more clutter-free radar holograms of an imaged surface can be obtained, particularly when penetrating materials to image interior image planes, or slices. The range-gating enables stacked hologram technology, where multiple imaged surfaces can be stacked in the downrange direction.

In U.S. Patent Application Publ. no. 2010/0214158, McEwan discloses an RF magnitude sampler for holographic radar. McEwan describes that the RF magnitude sampler can finely resolve interferometric patterns produced by narrowband holographic pulse radar.

In U.S. Patent Application Publication No. 2014/0024917, McMahon et al. describe a sensor for physiology sensing that may be configured to generate oscillation signals for emitting radio frequency pulses for range gated sensing. The sensor may include a radio frequency transmitter configured to emit the pulses and a receiver configured to receive reflected ones of the emitted radio frequency pulses. The received pulses may be processed to detect physiological characteristics such as bodily movement, sleep, respiration, and/or heartbeat.

(B) Periodic Limb Movement

Periodic Limb Movement (PLM) is a sleep disorder characterized by rhythmic movements of the limbs during sleep. The movements typically involve the legs, but upper extremity movements may also occur. Movements occur periodically throughout the night, such as every 30-40 seconds, and can fluctuate in severity from one night to the next. They tend to cluster in episodes known as PLM series that last anywhere from a few minutes to several hours.

Restless Legs Syndrome (RLS) is a neurologic sensorimotor disorder that is characterized by an overwhelming and unpleasant urge to move the legs while at rest. These sensations keep many people from falling asleep since they constantly want to move their legs. RLS affects approximately 10% of adults in the United States. Researchers believe that RLS may be confused with depression, and is commonly unrecognized or misdiagnosed as insomnia or other neurological, muscular or orthopedic condition. More than 80 percent of people with RLS also suffer from PLM—accounting for 8% of the population. Although RLS and PLM are closely linked, they are distinct clinical phenomena, hence it is possible to suffer from PLM but not RLS, suggesting that the prevalence of PLM is likely to exceed 8% of the population.

The current criteria for the scoring of a limb movement as a belonging to a PLM series excludes those limb movements associated with respiratory events (i.e., respiratory-related limb movements, or RRLMs). The rationale underlying this convention seems to be that RRLMs are provoked by respiratory-related arousals, and because of the periodic nature of obstructive respiratory events, they "mimic" PLMs. Thus, RRLMs are considered distinct from PLMs that occur as part of the phenotypic spectrum of restless legs syndrome.

RLS affects both men and women, can start at any age and can run in families. In addition, the severity of the disorder appears to increase with age. Older patients experience symptoms more frequently and for longer periods of time. (See, http://www.nindsnih.gov/disorders/restless_legs/detail_restless_legs.htm).

PLM had been shown to be more prevalent in patients with congestive heart failure (Hanly and Zuberi-Khokhar, 1996), however it is not clear how PLM impacts cardiovascular health.

Untreated PLM can affect quality of life, due to poor sleep and daytime sleepiness. For example, evidence has shown that sleep deprivation adversely alters the balance of leptin and ghrelin, two hormones which are significantly involved with the body's appetite control system. Voluntary sleep deprivation over a period of time (due to lifestyle choice) has been correlated with increased Body-Mass-Index (an indicator of obesity). Hence, objective measurement and control of sleep patterns may play a role in weight management.

Recent research has shown an increased mortality in patients with congestive heart failure (CHF) and end-stage renal disease when there is a concomitant diagnosis of PLM. Specifically, a vast body of literature has been published in the last few years looking at the association between PLM and cardiovascular disease. It has been postulated that arousals associated with PLMs may activate the sympathetic adrenergic system resulting in heart rate and blood pressure elevations, and thereby predisposing to adverse cardiovascular events. The diagnosis of PLM is of significant importance as it is linked to various cardiovascular diseases.

The gold standard method to detect and diagnose PLM is polysomnography (PSG) using bilateral electromyography (EMG) to detect muscle activity in the left and right tibialis anterior muscles. This is a very effective method, but it is highly expensive and requires to patient to sleep in a hospital sleep lab, wearing multiple uncomfortable sensors. In addition, monitoring patients over consecutive number of nights is of significant importance, as the PLM index has also been reported to vary from one night to another. This in turn makes the diagnosis of PLM more difficult, especially for longitudinal studies as that will incur significant costs and labour to perform the PSG studies.

Further methods for detecting and diagnosing PLM require full clinical evaluation of sleep patterns relying on electroencephalograph (EEG) monitoring, often requiring a hospital stay.

Accordingly, a method, system or apparatus which can reliably monitor sleep patterns, and movements during sleep, would have utility in a variety of settings. A system to unobtrusively detect and diagnose PLM in the home environment would be a valuable tool. Thus, there may be a need to improve sensors and processing such as for detection of particular movements such as periodic limb movement.

SUMMARY OF THE TECHNOLOGY

One aspect of some embodiments of the present technology relates to a sensor for detecting particular bodily movements, such as bodily movements related to sleep disorders.

An aspect of some embodiments of the present technology relates to a sensor for detecting a particular bodily movement with radio frequency signals.

Another aspect of some embodiments of the technology relates to such a sensor with a circuit configured to generate pulsed radio frequency (RF) signals such as for bodily movement type detection.

Some versions of the present technology include a radio frequency motion sensing apparatus for detection of periodic limb movement in a sleeping person. The apparatus may include a radio frequency transmitter configured to emit radio frequency signals. The apparatus may include a receiver. The receiver may be configured to receive reflected ones of the emitted radio frequency signals. The receiver may be configured to process the received reflected ones of the emitted radio frequency signals to produce motion signals. The apparatus may include a processor. The processor may be configured to evaluate the motion signals. The processor may be configured to generate an indicator to identify occurrence of periodic limb movement in the motion signals based on the evaluation of the motion signals.

In some versions, the receiver may be configured to mix the received radio frequency signals with the emitted signals to produce the motion signals. The processor may be configured to measure a phase difference between the received radio frequency signals and the emitted signals. The motion signals may include in-phase and quadrature motion signals. The emitted radio frequency signals may include pulsed radio frequency oscillating signals. The evaluation may involve comparing the motion signals to a noise threshold. Portions of the in-phase and quadrature motion signals may be compared to a noise threshold. The processor may be configured to update an action counter based on the comparing. The processor may be configured to increase the action counter when a portion of the motion signal is greater than the noise threshold. The processor may be configured to decrease the action counter when a portion of the motion signal is less than the noise threshold. The noise threshold may be defined as a frequency range in-band power of noise of the motion signal. The frequency range may be or include a range of four Hertz to eight Hertz. The processor may be configured to update the noise threshold based on determined average noise of the motion signals. The processor may be configured to detect a movement incident based on a comparison of a determined action count and a count threshold. The processor may be configured to determine a velocity of the movement incident. The processor may determine, or be configured to determine, the velocity based on a difference between the phase of the motion signals at adjacent samples. The processor may determine, or be configured to determine, displacement based on the determined velocity. The processor may determine, or be configured to determine, mean displacement from absolute values of determined velocities. The processor may characterize, or be configured to characterize, the movement incident based on a determined mean displacement of the movement incident. The processor may generate, or be configured to generate, a mapped activity value from the mean displacement.

In some versions, the evaluation of the processor may involve calculating and assessing a plurality of features derived from the motion signals. The plurality of features may include at least one of the following: a duration of a movement incident; a total activity of a detected movement incident; a mapped total activity of a detected movement incident; a cross-correlation of in-phase and quadrature motion signals of the motion signals during a detected movement incident; and a mean of a four quadrant inverse tangent function of real parts of in-phase and quadrature motion signals of the motion signals during a detected movement incident.

In some versions, the assessing may involve logistic regression and the indicator may include a probability value representing a likelihood of periodic limb movement during sleep.

In some versions, to evaluate the motion signals, the processor may be configured to: partition the motion signals into breath sections; classify each breath section of the motion signals as containing a limb movement or not containing a limb movement; and generate the indicator based on the classified breath sections. The processor may be further configured to pre-process the motion signals before the partitioning to de-trend and smooth the motion signals. The processor may be further configured to combine the motion signals to form a combined signal. The processor may be configured to perform principal component analysis to combine the motion signals. The processor may be further configured to discard periods of absence from the combined signal before the partitioning. The processor may be configured to detect zero-crossings of the combined signal to perform the partitioning. The processor may be configured to extract a waveform length feature from each breath section to perform the classifying. In some cases, to generate the indicator, the processor may be configured to score the breath sections containing limb movements as part of a periodic limb movement (PLM) series according to scoring criteria. In some cases, to generate the indicator, the processor may be configured to count limb movements forming part of a PLM series from a night's sleep session.

Some versions of the present technology may include a method for detecting periodic limb movement by a sleeping person. The method may include emitting, by a radio frequency transmitter, radio frequency signals toward the person. The method may include receiving, by a receiver, reflected ones of the emitted radio frequency signals. The method may include processing, by the receiver, the reflected ones of the emitted radio frequency signals to produce motion signals. The method may include, such by or in a processor, evaluating the motion signals and generating an indicator to identify occurrence of periodic limb movement present in the motion signals based on the evaluation of the motion signals.

In some versions, the received radio frequency signals are mixed with emitted signals to produce the motion signals. The processor may measure a phase difference between the received radio frequency signals and the emitted signals. The motion signals may include in-phase and quadrature motion signals. The emitted radio frequency signals may include epulsed radio frequency oscillating signals. The evaluating may include comparing the motion signals to a noise threshold. Portions of the in-phase and quadrature motion signals may be compared to a noise threshold. The method may include updating an action counter based on the comparing. The method may include increasing the action counter when a portion of the motion signal is greater than the noise threshold. The method may include decreasing the action counter when a portion of the motion signal is less than the noise threshold. The noise threshold may be defined as a frequency range in-band power of noise of the motion signal. The frequency range may be or include a range of four Hertz to eight Hertz. The method may include adjusting the noise threshold based on determined average noise of the motion signals.

In some versions, the processor may detect a movement incident based on a comparison of a determined action count and a count threshold. The processor may determine a velocity of the movement incident. The processor may determine the velocity with a difference between the phase of the motion signals at adjacent samples. The processor may determine displacement based on the determined velocity. The processor may determine mean displacement with absolute values of determined velocities. The processor may characterize the movement incident based on a determined mean displacement. The processor may compare the determined mean displacement to a threshold and generates a mapped activity value with the mean displacement.

In some versions, the evaluation may include calculating and assessing a plurality of features derived from the motion signals. The plurality of features may include at least one of the following: a duration of a movement incident; a total activity count of a detected movement incident; a mapped total activity of a detected movement incident; a cross-correlation of in-phase and quadrature motion signals of the motion signals during a detected movement incident; and a mean of a four quadrant inverse tangent function of real parts of in-phase and quadrature motion signals of the motion signals during a detected movement incident.

In some versions, the assessing may include logistic regression and the indicator may include a probability value representing a likelihood of periodic limb movement during sleep. The evaluating may include any one or more of partitioning the motion signals into breath sections; classifying each breath section of the motion signals as containing a limb movement or not containing a limb movement; and generating the indicator based on the classified breath sections. The method may include pre-processing the motion signals before the partitioning to de-trend and smooth the motion signals. The method may include combining the motion signals to form a combined signal. The combining the motion signals may involve principal component analysis. The method may include discarding periods of absence from the combined signal before the partitioning. The partitioning may include detecting zero-crossings of the combined signal. The classifying may include extracting a waveform length feature from each breath section. The generating the indicator may include scoring the breath sections containing limb movements as part of a periodic limb movement (PLM) series according to scoring criteria. The generating the indicator may include counting limb movements forming part of a PLM series from a night's sleep session.

Some versions of the present technology may include a periodic limb movement detection system. The system may include means for emitting radio frequency signals. The system may include means for receiving reflected ones of the emitted radio frequency signals. The system may include means for processing the received radio frequency signals to produce motion signals. The system may include means for evaluating the motion signals. The system may include means for generating an indicator to identify occurrence of periodic limb movement in the motion signals based on the evaluation of the motion signals.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which.

DETAILED DESCRIPTION

Monitoring of movement during sleep is of interest for many reasons from clinical monitoring of obstructive sleep apnea (OSA) to screening for periodic limb movement (PLM). In this regard, common sleep disorders in adults include Periodic Limb Movement (PLM) and Restless Legs Syndrome (RLS). In PLM, a subject may make characteristic repetitive limb movements (usually of the leg) every 30-40 seconds, leading to sleep disruption due to frequent awakenings. In RLS, the subject has an overwhelming desire to move or flex their legs as they fall asleep, again leading to disrupted sleep patterns. Spouses may complain that their partners kick their legs during sleep. Patient may report sleep onset problems or frequent arousals because of these movements. In contrast, those who are unaware of these movements may simply complain of un-refreshing sleep, or 'leg tiredness' on awakening in the morning.

Detection of these unusual body movements is important to confirming the diagnosis of these conditions and initiating treatment. In addition, significant changes in an indicator of the severity of PLM may act as a predictor of exacerbations in CHF patients.

Furthermore, detecting PLMs can enhance the accuracy of OSA monitoring by discarding PLMs which might otherwise corrupt the scoring of obstructive events.

Example scoring criteria for detection of PLM series may be as follows:

- Leg movements in a PLM series should last more than 0.5 seconds and less than 5 seconds.
- There should be at least four leg movements in a PLM series.
- The time between leg movements in a PLM series should be between 5 and 90 seconds.
- When leg movements are recorded from both left and right tibialis anterior muscles, they should be separated by an interval of at least 5 seconds for them to be counted as two separate movements.
- Leg movements can either be associated with EEG arousals or in severe cases even overt arousals.

The diagnosis of PLM can be made when patients present with insomnia, tiredness and daytime sleepiness in the presence of a high PLM Index (PLMI). A PLMI may be calculated by counting the number of PLMs during a night's sleep and dividing that number by sleep time in hours. The resulting PLMI may then be used to determine a diagnosis and severity of a patient's PLM. For example, a PLMI reading of more than 5 and less than 25 may be considered mild; a PLMI reading of more than 25 and less than 50 may be considered moderate, and a PLMI reading of more than 50 may be severe.

Figure 1:
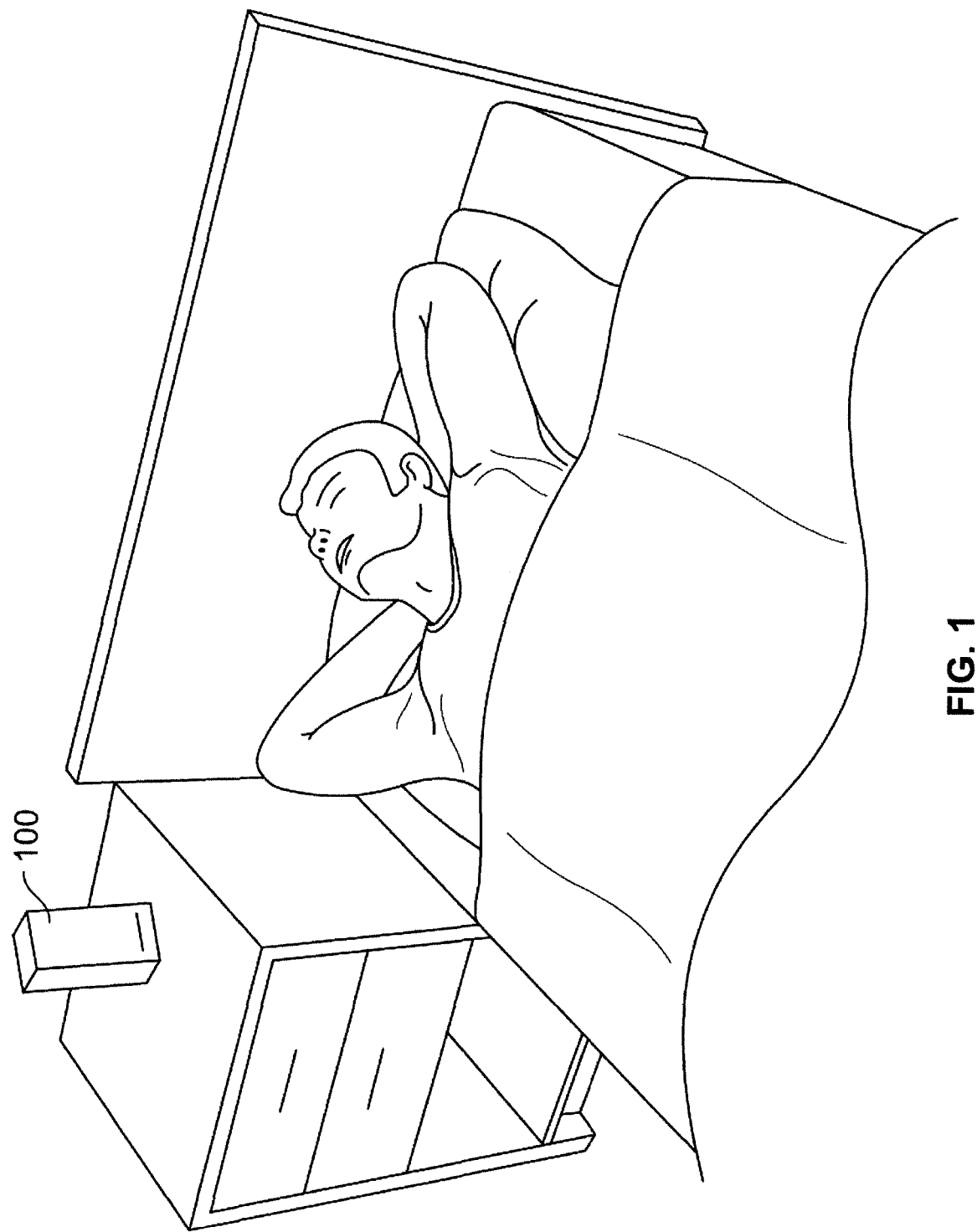
FIG. 1 is an illustration of an example PLM detection apparatus suitable for implementation with a radio frequency physiology sensor according to the present technology.

As illustrated in FIG. 1, some embodiments of the present technology may implement a sensing or detection apparatus 100, such as a non-contact sensor. Such a sensor may be implemented or configured with particular processing methodologies, useful for detecting particular motions of a user or a patient (the patient may be identical or a different person from the user of the apparatus 100) in the vicinity of the apparatus. The sensor may be a standalone sensor or may be coupled with other apparatus, such as a portable electronic device with processing and/or display functions, a respiratory treatment apparatus or sleep assessment apparatus. For example, a respiratory treatment apparatus may optionally provide an automated treatment response based on an analysis of the motion detected by the sensor of the apparatus. There is a potential association between PLM and sleep disordered breathing (SDB), which is often treated with continuous positive airway pressure (CPAP). For example, a respiratory treatment apparatus with a controller and a flow generator may be configured with the above-described sensor and may be configured to adjust a pressure treatment generated at a patient interface (e.g., mask) in response to particular motions detected by the sensor or avoid adjusting a pressure treatment in response to particular motions detected by the sensor. The respiratory treatment apparatus may be for example, a respiratory therapy or PAP apparatus, such as one described in International Patent Application Publication No. WO 2013/152403, the entire disclosure of which is incorporated herein by reference.

In general, detectable motions may be understood to be any that are intentionally or subconsciously made by a person rather than those physiological characteristics that are involuntarily periodic in nature and necessary for survival, (i.e., chest movement due to respiration or cardiac activity.) In this regard, motion signals sensed by a sensor that are generated by particular human motions may be processed to identify or characterize the particular movements. For example, a PLM may be detected through processing of the motion signals from a sensor. Particularized detection of such movements may then permit them to be counted, such as for generation of a PLMI.

A typical sensor, such as a radar sensor, of such an apparatus may employ a transmitter to emit radio frequency waves, such as radio frequency pulses for range gated sensing. A receiver, which may optionally be included in a combined device with the transmitter, may be configured to receive and process reflected versions of the waves. Signal processing may be employed, such as with a processor of the apparatus that activates the sensor, for PLM detection based on the received reflected signals.

Figure 2:
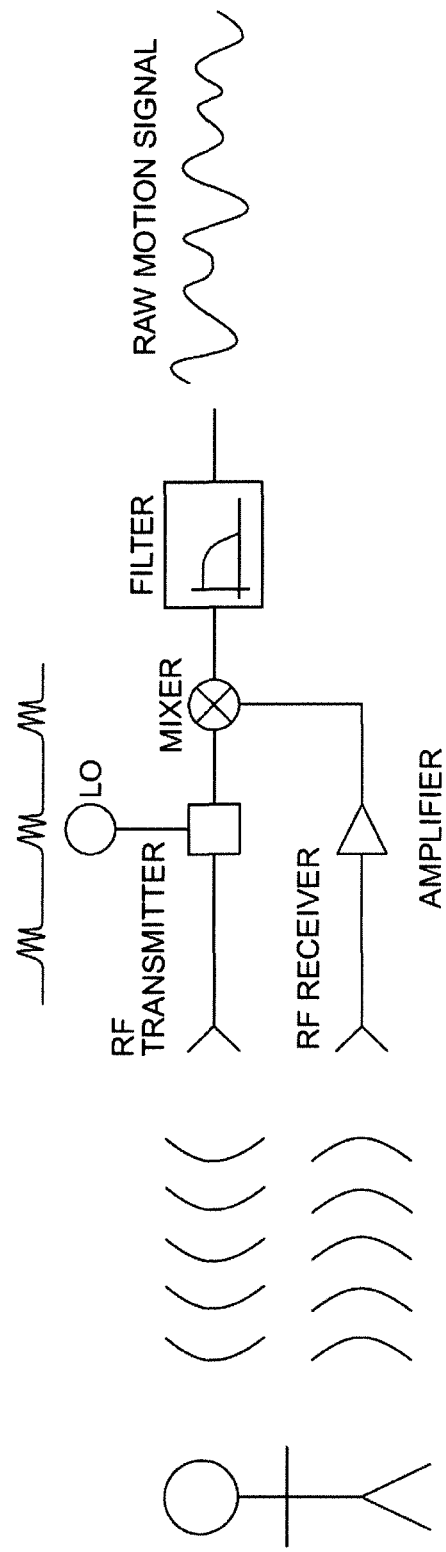
FIG. 2 is a diagram illustrating a conceptual structure and process flow for evaluation of sensor signals suitable for some embodiments of the present technology.

For example, as illustrated in FIG. 2, the transmitter transmits a radio-frequency signal towards a subject or patient, e.g., a human. Generally, the source of the RF signal is a local oscillator (LO). The reflected signal is then received, amplified and mixed with a portion of the original signal, and the output of this mixer may then be filtered. In some cases, the received/reflected signal may be demodulated by the transmitted signal, or the phase or time difference between them may be determined, for example, as described in US Patent Application Publication no. 2014-0163343A1, the entire disclosure of which is incorporated herein by reference.

Such a filtered demodulation signal may contain information about the movement (e.g., PLM), respiration and cardiac activity of the person, and may be referred to as a raw motion signal. In some cases, the raw motion signal may be processed to exclude involuntary periodic activity (e.g., respiration and/or cardiac activity) so that movement information in the signal may be classified for its particular movement type. In some cases, the sensor may be any of the sensors described in U.S. Patent Application Publication No. 2014/0024917, U.S. Patent Application Publication No. 2015/0216424 and U.S. Provisional Patent Application No. 62/205,129, the entire disclosures of which are incorporated herein by reference. Such sensors may be implemented by way of a set of processing steps that can be referred to as a movement processor. The movement processor provides an output signal, such as for detection of limb movement or PLM.

Figure 3:
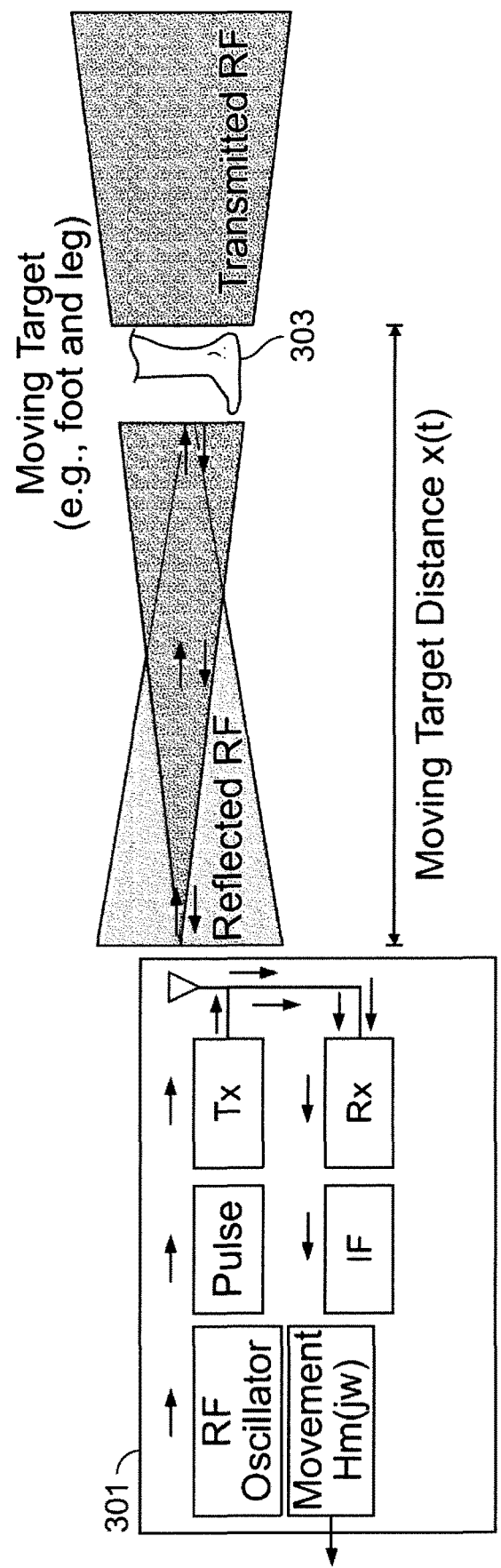
FIG. 3 is a block diagram of example processing for a sensor apparatus in some versions of the present technology.

For example, as shown in FIG. 3, sensor 301 can generate signals with different characteristics (e.g., different bandwidths, different sampling rates, etc.) for different evaluations. For example, the sensor 301 may generate, with a movement processor, a signal focused on targeted movements of a limb or leg 303. Thus, the sensor may implement analog and/or digital circuit components, for signal processing of the received sensor signal. This may optionally be implemented, at least in part, in one or more digital signal processors or other application specific integrated chips. In this regard, the sensor may be configured to generate oscillation signals with an RF Oscillator, for emitting radio frequency pulses (Pulse) for range gated sensing. The sensor may include a radio frequency transmitter (Tx) configured to emit the pulses and a receiver (Rx) configured to receive reflected ones of the emitted radio frequency pulses. The received pulses may be processed to determine an intermediate frequency (IF). The IF may then be used to determine a particular transfer function (Hm), which may be considered a movement processor or channel circuit for producing motion signals.

In one embodiment the sensor system may generate two analogue voltage signals (or their digital equivalent) which represent received in-phase (I) and quadrature (Q) channels of the sensor. For example, the sensor may operate by transmitting two short pulses of radio frequency energy at 10.5 GHz. The first pulse acts as the main transmit pulse, and the second pulse is the mixer pulse. The first pulse reflects off nearby objects to create an echo pulse that is received back in the sensor. By multiplying ('mixing') the echo pulse with the mixer pulse inside the receiver, a signal proportional to any phase shift of the echo pulse is generated. Moving objects (such as a leg or arm muscle tensing) may generate a variable phase shift that can be detected by the processing of the received signals such as in the circuits of the sensor or one or more integrated or coupled processors.

In some cases, the motion signals sensed by a sensor that are generated by a particular human movement may be processed to identify or characterize the particular movement. For example, movement within the motion signals may be detected by analysing the motion signals with a movement detection algorithm. Upon the detection of movement, the motion signals may be analysed to determine displacement and activity within the motion signals that are associated with the movement. Such activity and displacement measurements may form part of, or be a basis for, extracted features that may be indicative of PLM. Such features may include, for example, the duration of movements in the motion signals, activity during a movement, activity during a movement mapped to a pre-defined range of values, cross-correlation between phases of the motion signals during a movement, and mean of the four quadrant inverse tangent function of the real parts of the I and Q signals during each movement. These features are discussed in more detail herein. In some versions, the analysis of the motion signals, such as with a noise threshold, may involve automatic gain control to improve the accuracy of the movement detection.

These extracted features may then be analysed, such as by evaluation with one or more thresholds to detect incidents of PLM. For example, based on the determined features, the processor may assess whether the PLMs occurred during sleep or while awake. In this regard, the calculated feature values may be evaluated, such as by logistic regression techniques, to provide a probability that the determined PLMs occurred during wake or sleep. Depending on the number of movements which are found to have occurred during sleep, a PLM diagnosis may be generated, such as by counting the number such sleep PLMs and comparing the number of sleep PLMs per hour of sleep to a threshold that may correspond to a PLMI indicative of PLM.

Figure 4:
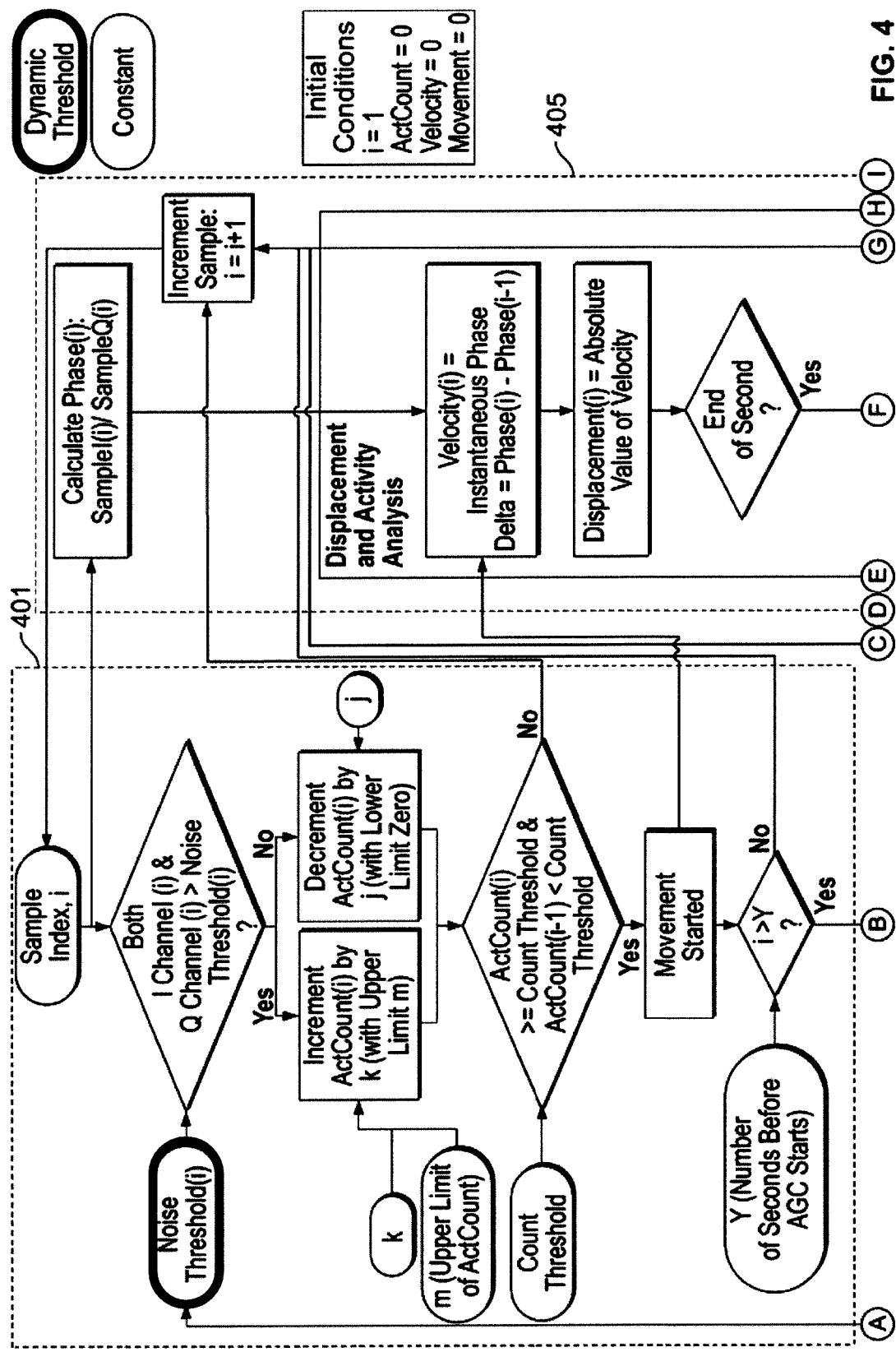
FIG. 4 is an example of an overall process flow for evaluation and processing of motion signals suitable for some embodiments of the present technology.
Figure 4:
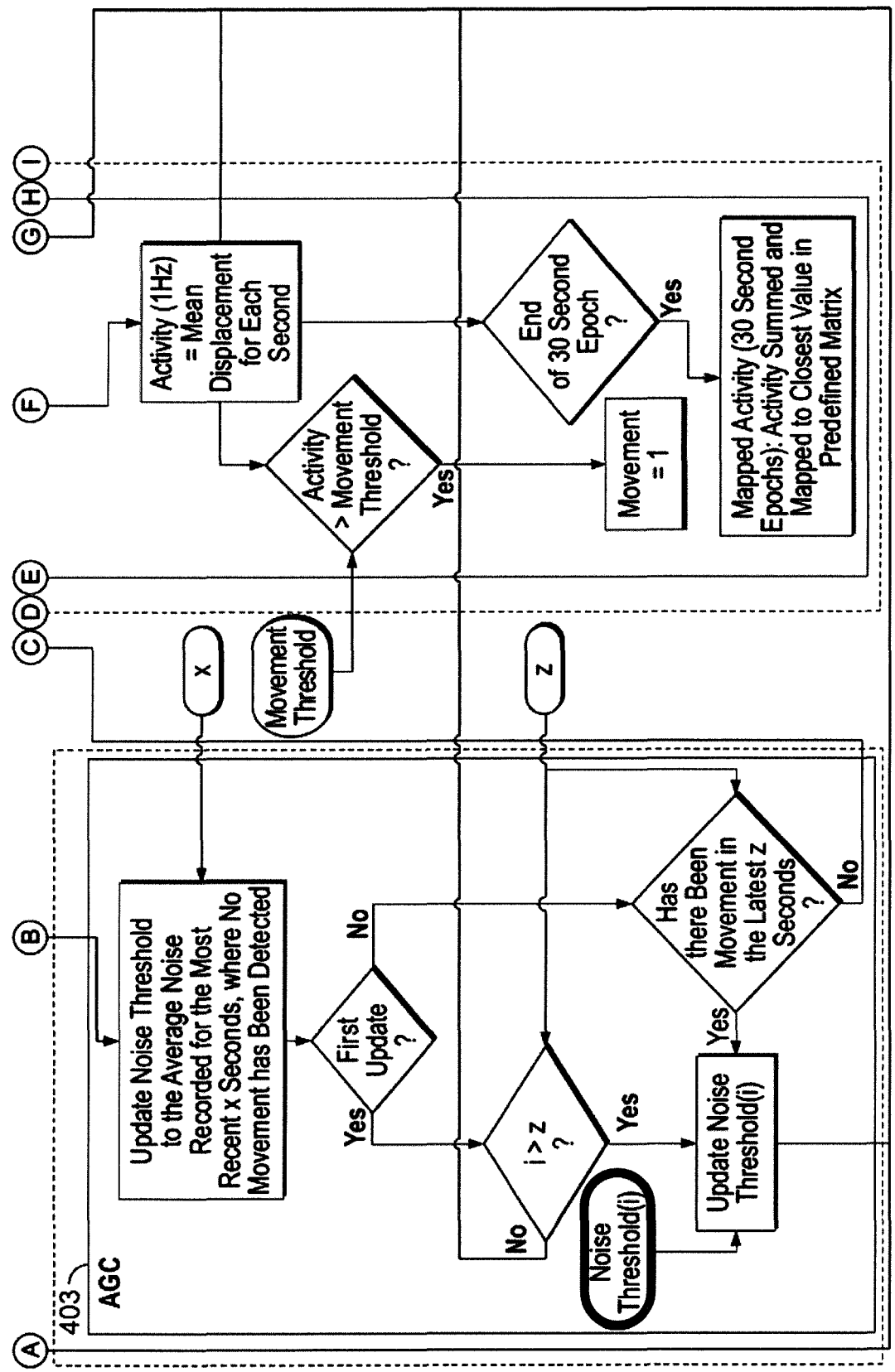

In FIG. 4, an overview processing flow diagram of a movement detector 401, automatic gain control 403, and displacement and activity analysis 405 is presented. The algorithms may be performed by an independent processor or by multiple modules and/or processors. As described in more detail below, samples of the signals of the sensors representing the I and Q channels from the sensor are initially processed through a movement detection algorithm of the movement detector 401. The samples of the I and Q signals may be captured at 16 Hz. An updated noise floor may be generated based on the noise of the signal when no movement is detected for a pre-set time period with the automatic gain control 403. Further, phase demodulation techniques may be used to map the non-contact sensor signal (16 Hz) to activity at 1 Hz, in a causal manner. Additional analysis may be carried out in epochs (e.g., a plurality of 30 second epochs) to provide an epoch-based total activity.

Figure 5:
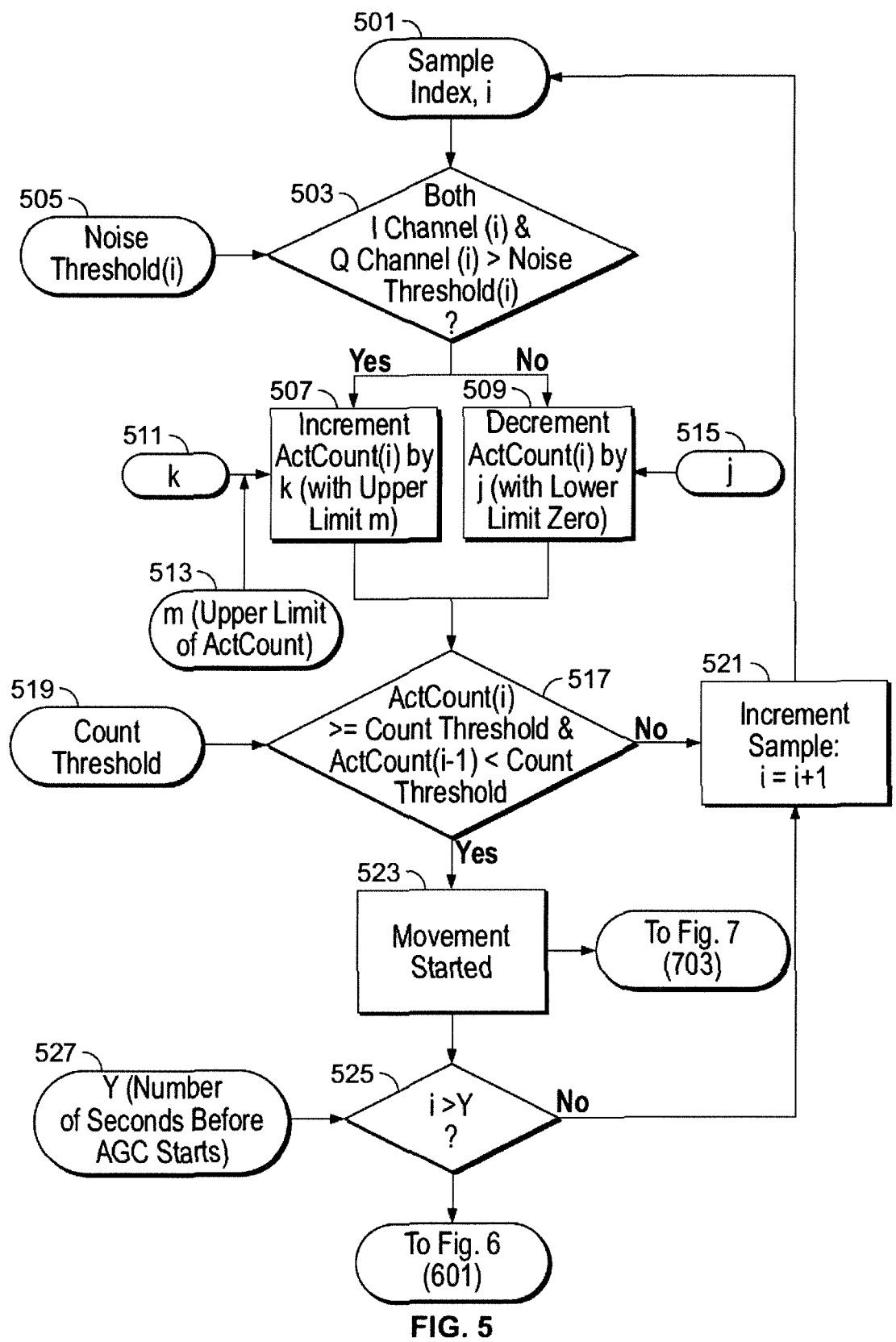
FIG. 5 is an example process flow for evaluation and processing of motion signals to determine movement suitable for some embodiments of the present technology.

The movement detection algorithm of the movement detector 401, as shown in processing diagram of FIG. 5, detects movement from the motion signals generated by the receiver of the sensor. The movement detection algorithm may be configured to run on a movement detection module. Initially, for each sample captured at time i of the I and Q motion signals (the "samples"), the movement detection algorithm may be performed, as shown in block 501. Time i may be pre-set to start at 1, for example. As shown in block 503, each sample of the motion signals may be compared to a noise threshold, represented by noise threshold(i) at block 505. In some embodiments the noise threshold 505 may be initially defined as the 4 Hz-8 Hz in-band power of the sensor noise signal. In some embodiments the noise threshold may be updated as more samples are processed, such as with an automatic gain control as further discussed below.

An action counter, as represented by ActCount(i), in FIG. 5, may track the number of samples at, above, or below the noise threshold. For example, when both the I and Q samples are greater than or equal to the noise threshold 505, the action counter may be incremented by a constant value 'k' 511, as shown in block 507. When both of the samples are below the noise threshold 505, the action counter may be decremented by another constant 'j' 515, as shown in block 509. The action counter may be subject to an upper limit 'm' 513, and a lower limit. In some embodiments the lower limit may be zero.

The action count may then be compared to a count threshold to detect a movement incident as shown at block 517. For example, when the action count at time i is greater than or equal to a count threshold 519, and the action count at time i−1 is below the count threshold 519, a movement incident determination may be made, as shown in block 523. Upon determining a movement incident has started, the samples may be passed to or processed by the displacement and activity analysis algorithm, described below in relation to FIG. 7. Otherwise, a movement incident determination may not be made and i may be updated to i+1, as shown at block 521. The algorithm may then restart, and process the samples captured at updated time i. These iterations may occur until all samples, or a portion of samples have been processed.

In some versions, a determination may be made whether to send or process the samples for an automated gain control (AGC). In this regard for each sample beyond first y seconds of recording with no movement detected, an analysis may be carried out on the noise. For example, the time the samples were captured, (i.e., i) may be compared to a predetermined number 527 'y' as shown in block 525. Predetermined y may represent a time period before the AGC begins to process samples. For samples that occur after the time period y, the samples may pass to or be processed by the AGC as further described below in relation to FIG. 6 below. Otherwise, the samples may not be so passed to or processed by the AGC, and i may be updated to i+1, as shown at block 521 (i.e., processing may iterate to the next sample(s)).

Figure 6:
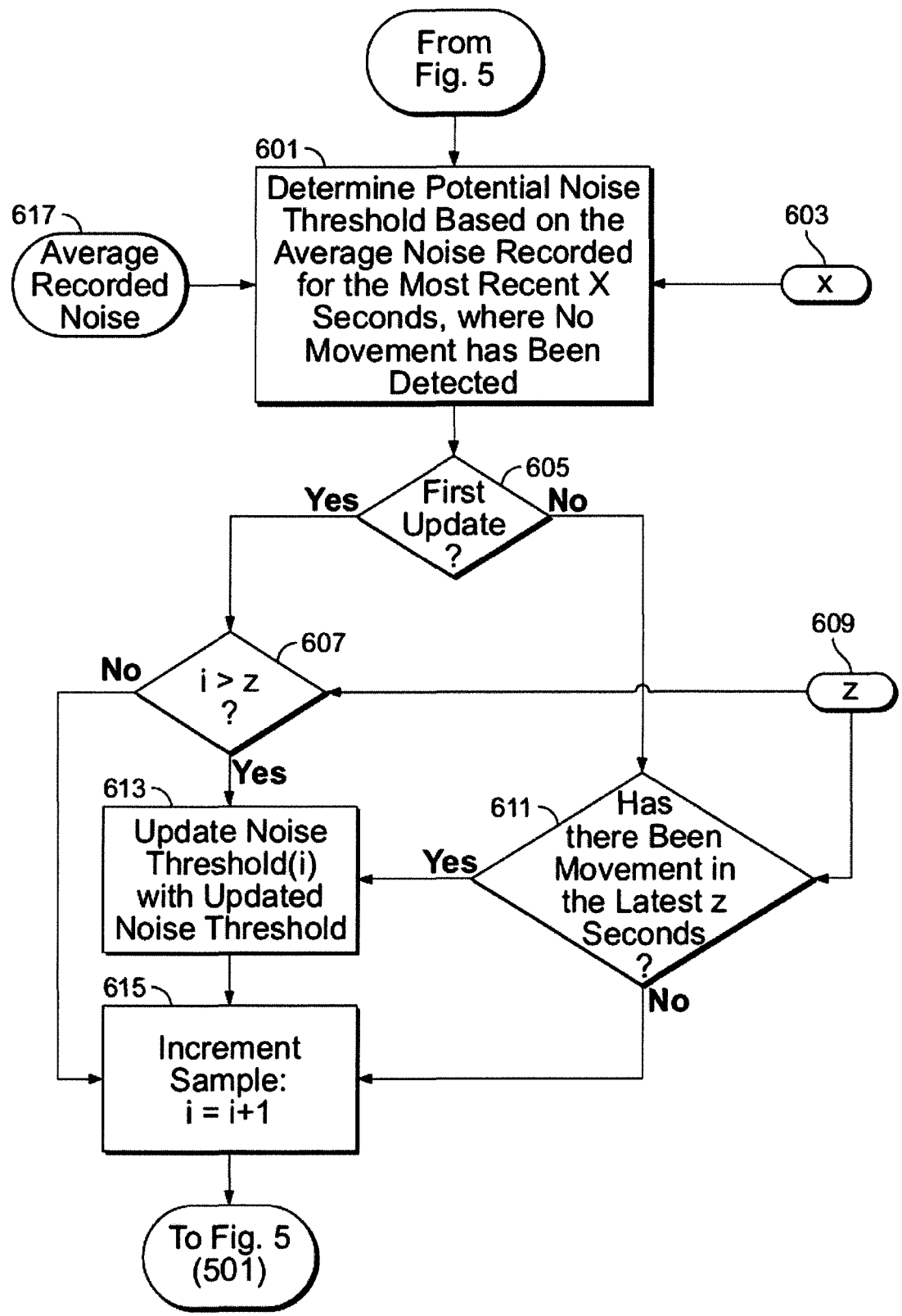
FIG. 6 is an example process flow for evaluation and updating of a noise floor suitable for the process flow of FIG. 5.

As shown in FIG. 6, the AGC module may update the noise threshold value used at block 503. In this regard, the AGC enables the movement detection module to adjust to a given recording's noise floor and allow for improved consistency across sensors and setup. For example, turning to block 601 the AGC may determine the average noise recorded in the samples 617 for the most recent 'x' seconds, where x 603 is a time period where no movement has been detected. A determination may also be made whether the noise threshold has been updated previously, as shown in block 605.

In the event the threshold has been previously updated, the AGC may determine whether there have been movements in the last 'z' seconds, where z 609 is a predetermined time period, as shown in block 611. In some embodiments z may be tenths of a second, seconds, minutes, hours, etc. As shown in block 613, when there have been movements in the last z seconds, the noise threshold may be updated to the average noise, as described in relation to block 601. Otherwise, when there have been no movements, the noise threshold may not be updated and i may be updated to i+1, as shown at block 615. The process may then proceed back to block 501 of FIG. 5.

In the event the threshold has not been previously updated (e.g., the first update of the noise threshold) i may be compared to z as shown in block 607. When i is greater than z the noise threshold may be updated as shown in block 614 to the average noise, as described in relation to block 601. Otherwise, when i is less than or equal to z, the noise threshold may not be updated, and i may be updated to i+1, as shown at block 615. The process may then proceed back to block 501 of FIG. 5.

Figure 7:
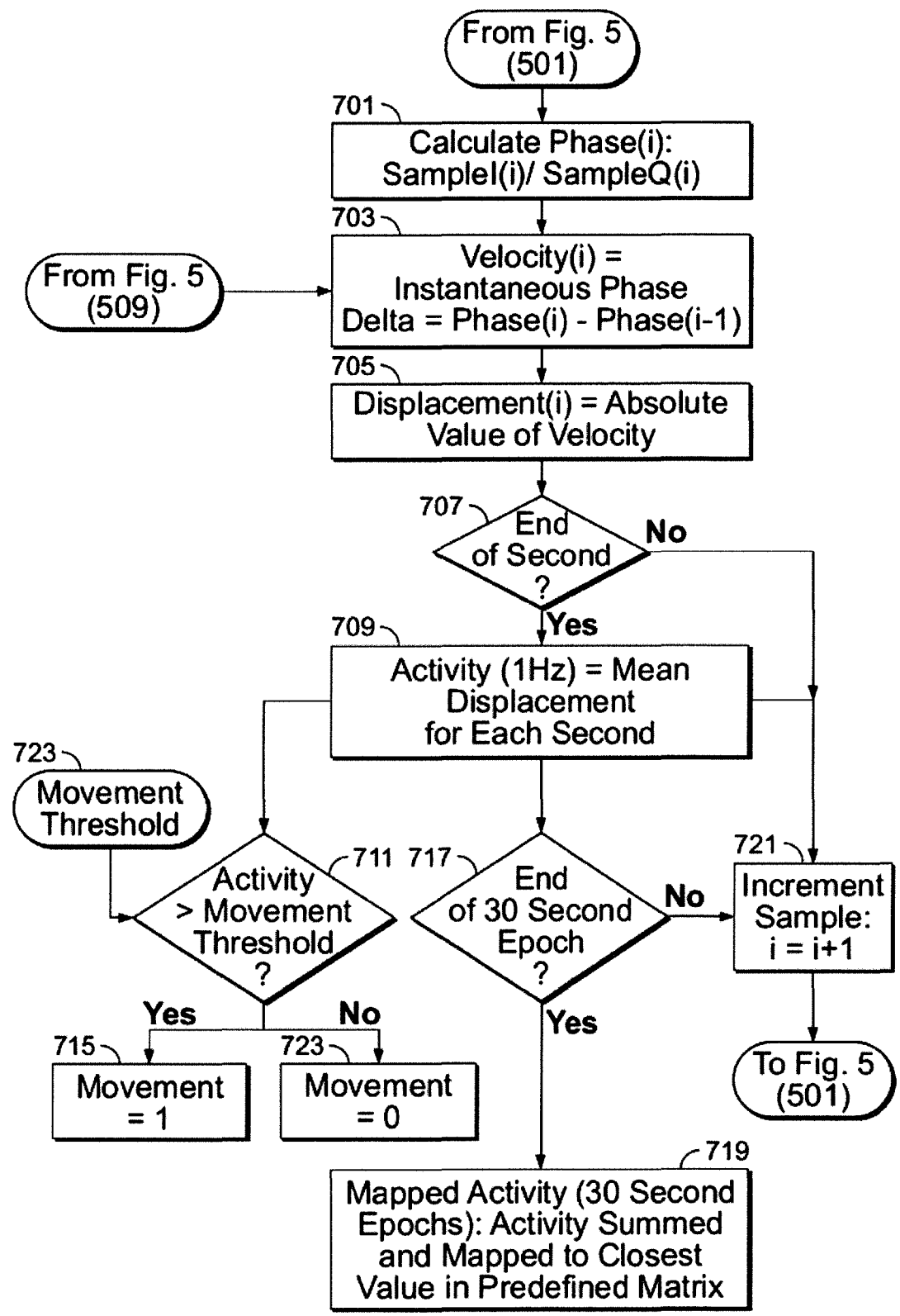
FIG. 7 is an example process flow for evaluation of motion signals to determine activity and mapped activity suitable for the process flow of FIG. 5.

Turning now to FIG. 7, a displacement and activity analysis algorithm is shown. The displacement portion of the algorithm may be implemented to determine the amount of activity of a detected movement incident of the motion signals such as phase, velocity, and displacement within the motion signals. For example, as shown in block 701 of FIG. 7, the phase of the I & Q channel samples at time i may be found (e.g., from a ratio of the in-phase and quadrature signals). In some cases, the phase may be a mapped phase by mapping a ratio of the I and Q samples (e.g., SampleQ(i)/SampleI(i)) to the closest value in a pre-defined matrix of arc-tangent values. The pre-defined matrix of arc-tangent values may be stored within a memory accessible to a processor of the sensor. The pre-defined matrix of arc-tangent values may be used to reduce the amount of processing. An example pre-defined matrix of arc-tangent values is shown in Table 1, below.

TABLE 1

Arc-tangent matrix

| Ratio of the Motion Signals | Map to this Value |
|---|---|
| −1*10^10 | −4/8*π |
| −2.4142 | −3/8*π |
| −1 | −2/8*π |
| −0.4142 | −1/8*π |
| 0 | 0 |
| 0.4142 | 1/8*π |
| 1 | 2/8*π |
| 2.4142 | 3/8*π |
| 1*10^10 | 4/8*π |

Upon detection of a movement incident (e.g., movement detector 401), as described in relation to block 523 in FIG. 5, velocity and displacement of the samples may be determined from the phase difference between the samples. For example, as shown in block 703, velocity may be calculated as the change in phase between consecutive samples (e.g., an instantaneous phase delta). For example, velocity at time i may be calculated by subtracting the phase of the samples captured at time i−1 from the phase of the samples captured at time i. As shown in 705, displacement at time i may be found by taking the absolute value of the velocity value at time i. In this regard, displacement may be an intermediate variable calculated as per block 705, which may have a sampling rate of 16 Hz. Displacement may be calculated from velocity, which may be calculated from the raw motion signal, each being a variable with a sampling rate of 16 Hz.

Based on the phase, velocity, and displacement of the motion signal, activity analysis may be performed. Activity analysis may be implemented for creation of classification features that can be representative of the movement incident type. Initially, as shown in block 707, the activity portion of the algorithm may determine whether one second's worth of samples has been processed by the displacement algorithm, as shown in block 707. In the event one second of activity has been processed, the mean displacement of the samples within the one second window may be determined. For example, the mean displacement for each one second window may be determined by averaging the displacement values of each sample which occurred during one second window, as shown in block 709. In the event a second of activity has not been processed, the sample may be incremented by 1, as shown in block 721. In some embodiments the mean displacement for each one second window may be referred to as activity.

The length of time over which a movement incident occurs may be determined from the calculated activity (i.e., the mean displacement for each one second window). In this regard, as shown in block 711, the activity may be compared to a movement threshold 713. When the activity is greater than the movement threshold, a binary movement vector may be updated to indicate movement. For example, a binary movement vector may be updated to 1 (true) when movement is detected and 0 (false) if no movement is detected, as shown in block 715 and 723, respectively.

The movement threshold may be fixed, at least initially, or it may be determined by the AGC. For example, the variance of noise may be estimated based on the estimated variance from the previous sample and how much the current noise value differs from the previous average noise. The movement threshold may then be calculated once z seconds have been recorded. The movement threshold may be obtained by taking the current average noise level (a) and adding three times the estimated variance of the noise level (b) and multiplying the result by a safety margin coefficient (a constant, e.g. 1.5). Once the movement threshold has been updated the AGC analysis may be reset and the movement threshold will not be updated until z seconds with no movement having taken place. In some embodiments, the movement threshold may be programmed so that spurious, low level movements which may satisfy the initial movement determination fail to satisfy the movement threshold.

The total activity may be determined in epochs. For example, each epoch may be a number of seconds, such as thirty seconds. As shown in block 717 the activity portion of the algorithm may determine whether an epoch has occurred (e.g., thirty seconds of samples have been processed). At the end of each such epoch, the total activity may be determined by summing the activity (e.g., mean displacements) for each second within the epoch as shown in block 719. To assist in computational efficiency, total activity may optionally be mapped to the closest value on a pre-defined matrix, such as the example matrix in Table 2, below.

TABLE 2

Activity Mapping Matrix

| | Compare total activity for epoch with | | | |
|---|---|---|---|---|
| | $22 \times 10^{-4}$ | $55 \times 10^{-4}$ | $11 \times 10^{-3}$ | $55 \times 10^{-3}$ |
| Map to this value | 0 | 1 | 2 | 2.5 |

Upon performing the activity analysis i may be updated to i+1, as shown at block 721. The process may then proceed back to block 501 of FIG. 5 to process the next sample (e.g., the process iterates to the next sample).

Figure 8:
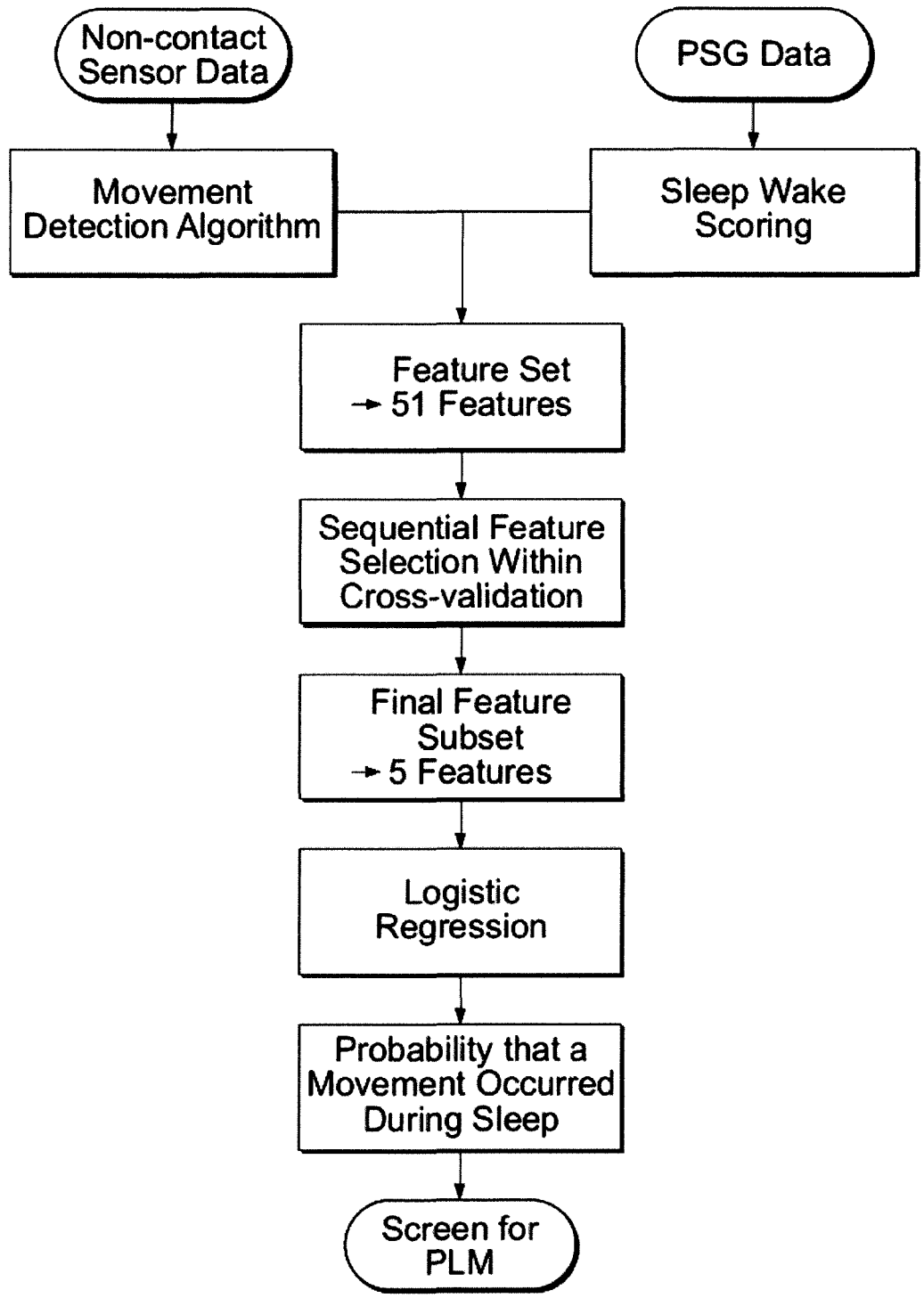
FIG. 8 is an example process flow diagram illustrating a training process for movement classification in accordance with versions of the present technology.

For each movement incident (e.g., movement=1), features may then be determined based on the displacement and activity analysis. While any suitable set of features derived from non-contact sensor data may be calculated, sequential forward feature selection may be used, such as with ten-fold cross-validation to select a suitable subset of features that would combine using logistic regression to best identify whether a desired movement (e.g., a PLM) has occurred while the subject was asleep or awake. Such an example process is illustrated in FIG. 8.

In some versions, a set of one, more or all of the features that may be calculated to characterize the detected movement incident are shown in Table 3.

TABLE 3

Example features

| Feature | Description | Coefficient |
|---|---|---|
| Movement duration (sec) | Duration of movement incident in seconds. | 0.0399331771284082 |
| Activity (Speed of Change) | Total activity during a movement incident with a value in the range 0-30. | 0.0567345792614327 |
| Mapped activity | Total activity during a movement incident mapped to a pre-defined range of values between 0 and 2.5. | −0.130345006625921 |
| crosscorrMovement | Cross-correlation of the I and Q signals during a movement incident. This provides a measure of the similarity the I and Q signals during the movement incident. | −0.513047516838771 |
| meanAtanMovement | The mean of the four quadrant inverse tangent function of the real parts of the I and Q signals during a movement incident. The inverse tangent function acts on the I and Q signals element-wise to return AtanMovement, which is the same size as the sections of I and Q signals examined. The mean of AtanMovement is taken for each movement incident. | −0.0816012254889409 |
| Constant | Constant coefficient required by logistic regression. | −1.58093976269811 |

Turning to the first feature, movement duration, a binary movement vector is generated for each second during a movement incident by the aforementioned process and set to true (1) each second the activity is greater than the movement threshold. This vector may be analysed to determine the duration of the movement incident. In this regard, upon the movement vector switching to true (1), which indicates the start of the movement incident, the time period until the binary movement vector switches back to false (0) may be calculated. The total duration is the period from when movement is indicated until movement is not indicated. In some versions, such a duration may be measured in seconds.

The second feature may be activity, which was determined during the activity analysis, described in detail above. For example, each mapped activity value for an epoch of a movement incident may be summed, and the activity feature here may be the resulting value of the summation. In some versions, the activity feature may be capped at a value, such as thirty.

The third feature is mapped activity. As previously described, at the end of each thirty second epoch, the total activity may be determined by summing the activity values (mean displacement values) for each second within the epoch as shown in block 719, of FIG. 7. The total activity values may then mapped to the closest value on a predefined matrix as defined in Table 2. In some embodiments the total activity value may be capped at a value, such as thirty.

The fourth feature is cross-correlation of the I and Q signal samples during a detected movement incident. Such a measure provides the similarity between the I and Q signals during such an incident. Such cross-correlation of the I and Q samples during a movement incident may be determined using known cross-correlation calculations.

A fifth feature may be the MeanAtanMovement. The MeanAtanMovement may be the mean of the four quadrant inverse tangent function of the real parts of the I and Q signals during each movement incident. The inverse tangent function acts on the I and Q signals element-wise to return AtanMovement, which is the same size as the sections of I and Q examined. The mean of AtanMovement is taken for each movement incident.

The features may be combined in an evaluation employing logistic regression to provide a probability that each movement incident occurred during wake or sleep. Optionally, for each feature during a movement incident, the features may be multiplied by a coefficient such as the example values shown in Table 3. Additionally, a constant coefficient may also be used in the logistic regression. An example constant coefficient value is also shown in Table 3. If the output of the logistic regression classifier is less than some probability threshold, for example 35%, the movement incident may be considered to have occurred during sleep. Otherwise, the movement incident may be considered to have occurred during wake, and may be ignored.

A classifier, as described below, may be defined by a set of coefficients as described in Table 3. The classifier may be trained using logistic regression methods (e.g., a generalized linear model, assuming a binomial distribution and using a Bernoulli distribution as link function between the linear predictor and the mean of the distribution function). The overall classifier output may be obtained by:

Calculating the sum of the product between each feature and associated coefficient ("sumVal"); and Calculating the classifier output as the inverse of (1+e^sumVal) where 'e' is the mathematical constant of the base of a natural logarithm.

The classifier output may then be compared against a set threshold (e.g., 35%, or more or less) to identify whether a movement incident is likely to have occurred during sleep or not.

The movement incidents which are deemed to have occurred during sleep and form part of a PLM series may then be used for screening subjects who may have PLM. For example, as previously described, a diagnosis of PLM may be made when patients present with insomnia, tiredness and daytime sleepiness in the presence of a high PLM index (PLMI). The PLMI may be calculated by counting the number of PLMs (e.g., sleep movement incidents detected by the aforementioned classification process that are scored as part of a PLM series) and dividing that number by sleep time in hours. The resulting number may then be used to determine a diagnosis and severity of a patient's PLM. For example, a PLMI reading of more than 5 and less than 25 per hour may be considered mild; a PLMI reading of more than 25 and less than 50 per hour may be considered moderate, and a PLMI reading of more than 50 per hour may be severe.

In some versions, instead of or in addition to using the total number of movement incidents during sleep as a sole indicator of PLM, a processor may also or alternatively be configured to calculate and/or implement:

Percentage of movement incidents during sleep. For example, duration of periods of sleep movement incidents may be calculated relative to total sleep time to generate a PLM indicator as a percentage. Note that this highly correlates with PLM-related movements as very few non-involuntary periodic movements otherwise occur while subjects are asleep.

The total number of movement incidents during sleep per hour (or other timeframe, such as a shorter time frame). Such an indicator may be calculated along with evaluating the maximum/mean/range of this value. PLM sufferers tend to have clusters of movements at different points during the night. This is comparable to a PLM index definition from PSG, and would allow for a like-for-like comparison.

A combination of the above indicators, personal information (BMI, age, gender), and other sensor-derived features.

A measure of how PLM affects the sleep quality of a patient, by comparing prevalence of non-PLM movements immediately after a series of PLM movements with their prevalence in other sections of the night.

These other indicators may be directly obtained from parameters extracted using the methods disclosed so far and may further improve these results, providing a potentially more robust solution or allow returning comparable indices to those currently used in clinical practice (i.e., number of movement incidents/hour as an index).

Figure 9:
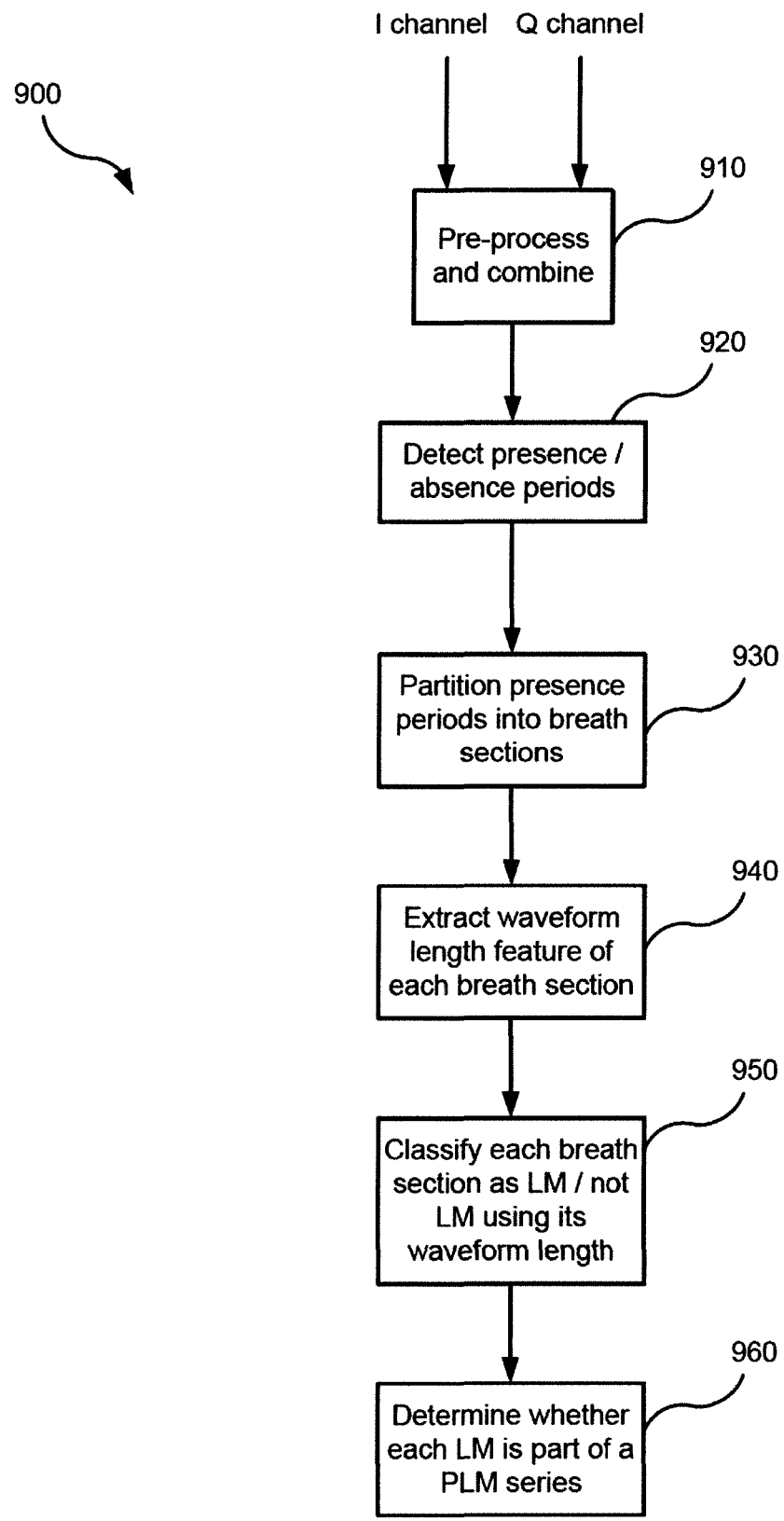
FIG. 9 is a flow chart illustrating a method that may be used to detect PLMs according to an alternative form of the present technology.

FIG. 9 is a flow chart illustrating a method 900 that may be used to detect PLMs according to an alternative form of the present technology. Like the method 400, the method 900 may be performed by an independent processor or by multiple modules and/or processors. Thus, the processor(s) may be configured with any one or more of the steps of the method(s).

The method 900 starts at step 910, which pre-processes the I and Q motion signals from the sensor and combines them to form a single signal. Step 920 analyses the combined signal to detect the presence or absence of a patient over time from the measurement zone of the sensor 301. Periods of absence may be characterized by an absence of patient related motion within the sensor signals. The periods of absence are discarded from further analysis. The remaining presence periods of the combined signal are then partitioned at step 930 into breath sections. Step 940 then extracts a feature known as the waveform length from the portion of the combined signal corresponding to each breath section. Step 950 classifies each breath section according to whether it does, or does not, contain a limb movement (LM) using the waveform length feature computed at step 940. Finally, step 960 applies scoring criteria such as those listed above to determine whether each detected LM forms part of a PLM series. Such scoring may consider an entire sleep session (e.g., a night's sleep session) so that the PLM series may represent an evaluation of all or most of the movement signals from a single sleep session.

Figure 10:
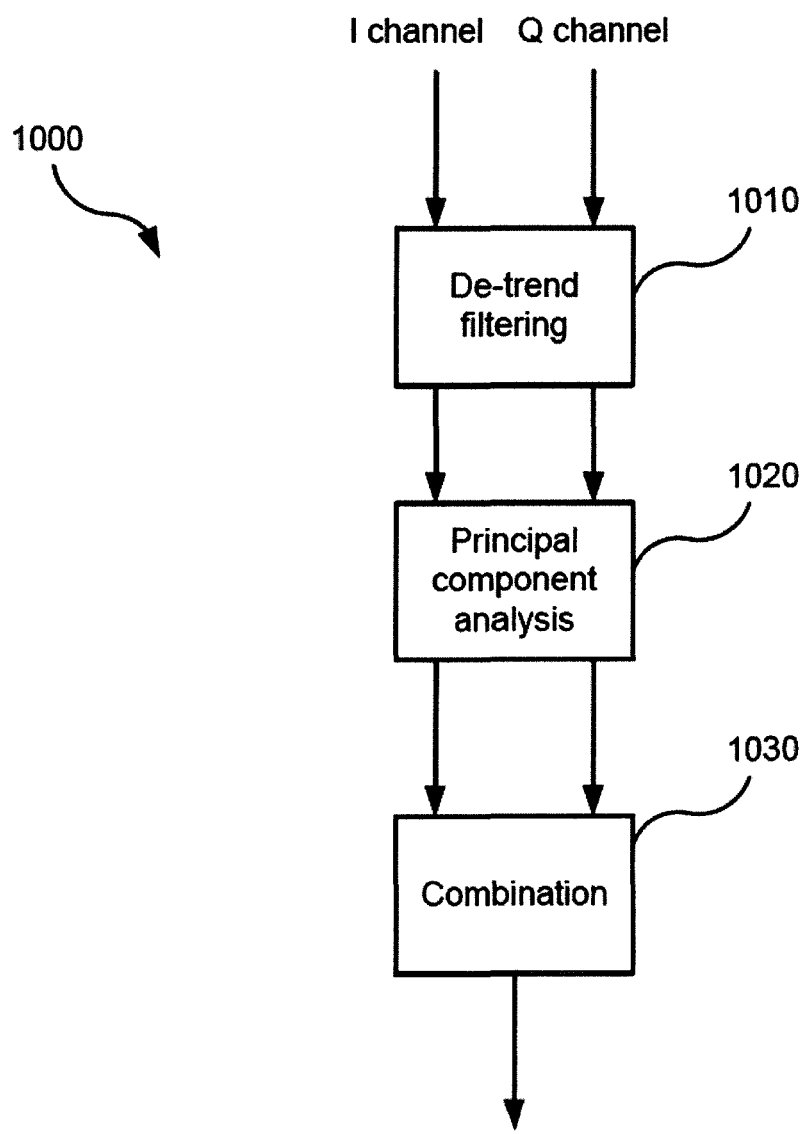
FIG. 10 is a flow chart illustrating a method that may be used to implement the pre-processing step of the method of FIG. 9.
Figure 11A:
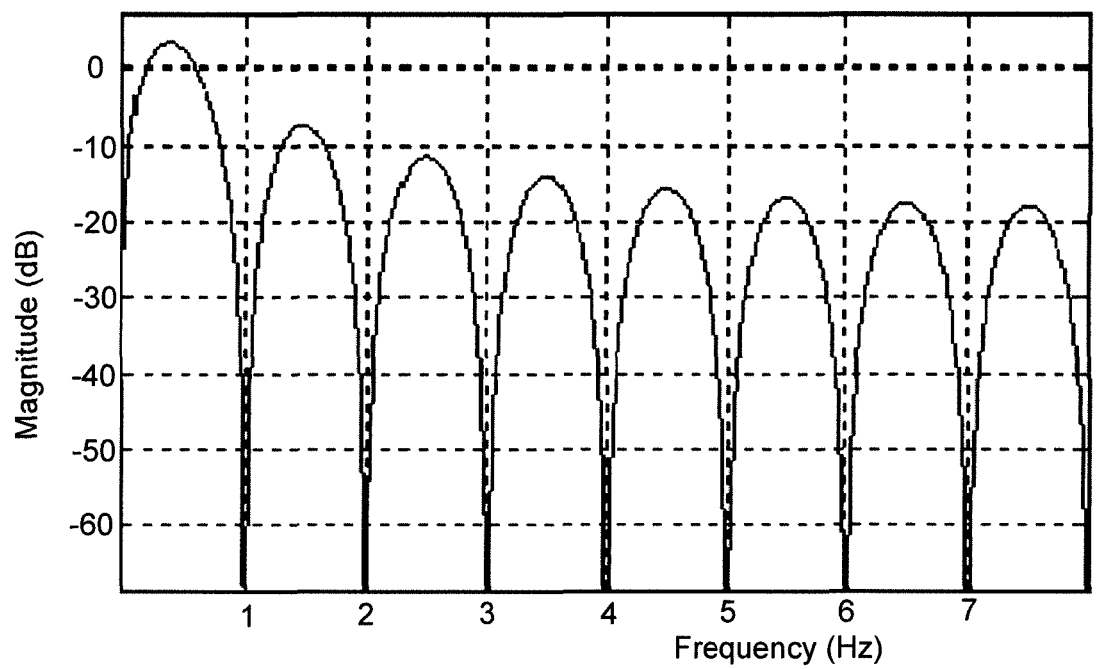
FIG. 11A illustrates the magnitude frequency response of a filter that may be applied at the filtering step of the method of FIG. 10.
Figure 11B:
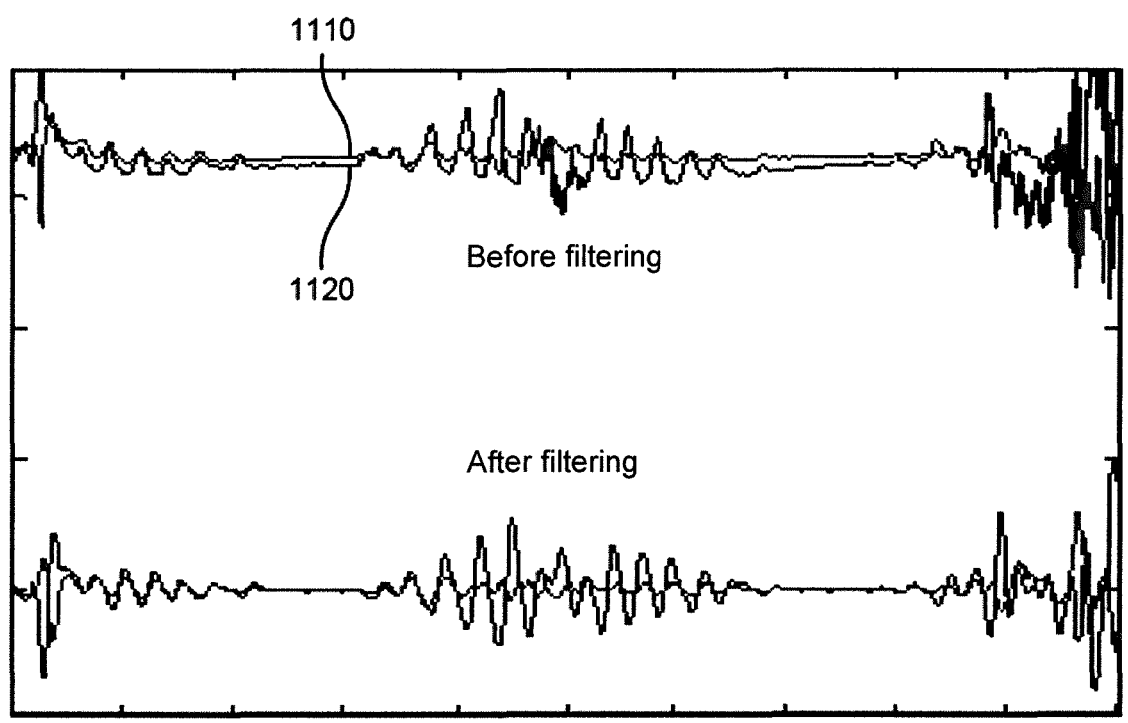
FIG. 11B shows the result of filtering example I and Q motion signals with the filter of FIG. 11A.

FIG. 10 is a flow chart illustrating a method 1000 that may be used to implement the pre-processing step 910 of the method 900 according to one implementation of the alternative form of the present technology. The method 1000 starts at step 1010 which applies a filter to de-trend and smooth each of the I and Q motion signals independently. The filter identifies ascending and descending slopes of the I and Q motion signals, and removes any baseline wandering and other low-frequency components from the I and Q motion signals that might affect the morphological features of the signals. FIG. 11A illustrates the magnitude frequency response of a filter that may be applied at step 1010. FIG. 11A shows that the filter is a bandpass filter with a peak around 0.4 Hz (24 cycles per minute) and low DC response to remove the mean of the I and Q motion signals. FIG. 11B shows the result of filtering example I and Q motion signals 1110 and 1120 with the filter of FIG. 11A. Before filtering, the I and Q motion signals 1110 and 1120 are DC shifted, and after filtering have corrected baselines as well as cleaner morphology.

After step 1010, the method 1000 proceeds to step 1020 which applies principal component analysis (PCA) to the filtered I and Q motion signals to project the signals into two principal components in which the first component has the majority of the energy (variance). In one implementation, PCA uses a singular value decomposition (SVD) of a data matrix of the filtered I and Q motion signals. Step 1030 then combines the two principal components into one signal which captures the total information contained in the original I and Q motion signals. In one implementation, step 1030 discards the lower-energy component of the two principal components from step 1020.

As described above, step 920 of the method 900 analyses the combined signal to detect the presence or absence of a patient over time from the measurement zone of the sensor 301. One implementation of step 920 applies an energy operator, such as the Teager energy or the root mean square (RMS), to the combined signal, and thresholds the energy signal. Periods where the energy is above a threshold are periods of presence, whereas periods where the energy is below a threshold are periods of absence.

In other implementations, step 920 uses a statistical approach based on L-moments. In statistics, L-moments are a sequence of statistics used to summarize the shape of a probability distribution. L-moments can be defined for any random variable whose mean exists, and form the basis of a general theory which covers the summarization and description of theoretical probability distributions, the summarization and description of observed data samples, estimation of parameters and quantiles of probability distributions, and hypothesis tests for probability distributions. L-moments are usually defined as linear combinations of conventional order statistics. For a real-valued random variable X with cumulative distribution $F(x)$ and quantile function $x(F)$ (the inverse function of $F(x)$), order statistics of a random sample of size n drawn from $F(x)$ are defined as $$EX_{j:r} = j \binom{r}{j} \int_0^1 x(F(x))^{j-1} (1 - F(X))^{r-j} dF(x) \quad \text{(Eq. 1)}$$

for $r=1, \ldots, n$ and $j=1, \ldots, r$. The L-moment $\lambda_r$ of order r ($r=1, 2, \ldots, n$) of X is defined as $$\lambda_r \triangleq r^{-1} \Sigma_{k=0}^{r-1} (-1)^k \binom{r-1}{k} EX_{r-k:r} \quad \text{(Eq. 2)}$$

L-moments can be used to calculate quantities analogous to standard deviation, skewness and kurtosis, termed the L-scale, L-skewness and L-kurtosis respectively (the L-mean is identical to the conventional mean). L-moments have the theoretical advantages over conventional moments of being able to characterize a wider range of distributions and, when estimated from a sample, of being more robust to the presence of outliers in the sample. Compared with conventional moments, L-moments are less subject to bias in estimation and approximate their asymptotic normal distribution more closely in finite samples. Parameter estimates obtained from L-moments are sometimes more accurate in small samples than even the maximum likelihood estimates.

Substituting Eq. 1 into Eq. 2, the L-moment $\lambda_r$ of order r ($r=1, 2, \ldots, n$) may be computed as $$\lambda_r = \int_0^1 x(F) P_{r-1}^*(F) dF \quad \text{(Eq. 3)}$$

where $P_n^*(F)$ is the n-th shifted Legendre polynomial of F, related to the usual Legendre polynomials $P_n(u)$ by $P_n^*(u) = P_n(2u-1)$. Using Eq. 3 and the definitions of Legendre polynomials, it may be shown that the first three L-moments may be computed as linear combinations of conventional order statistics:

$$\lambda_1 = EX_{1,1} = \int_0^1 x(F) dF \quad \text{(Eq. 4)}$$

$$\lambda_2 = \frac{1}{2}(EX_{2,2} - EX_{1,2}) = \int_0^1 x(F)(2F - 1) dF \quad \text{(Eq. 5)}$$

$$\lambda_3 = \frac{1}{3}(EX_{3,3} - 2EX_{2,3} + EX_{1,3}) = \int_0^1 x(F)(6F^2 - 6F + 1) dF \quad \text{(Eq. 6)}$$

Figure 12:
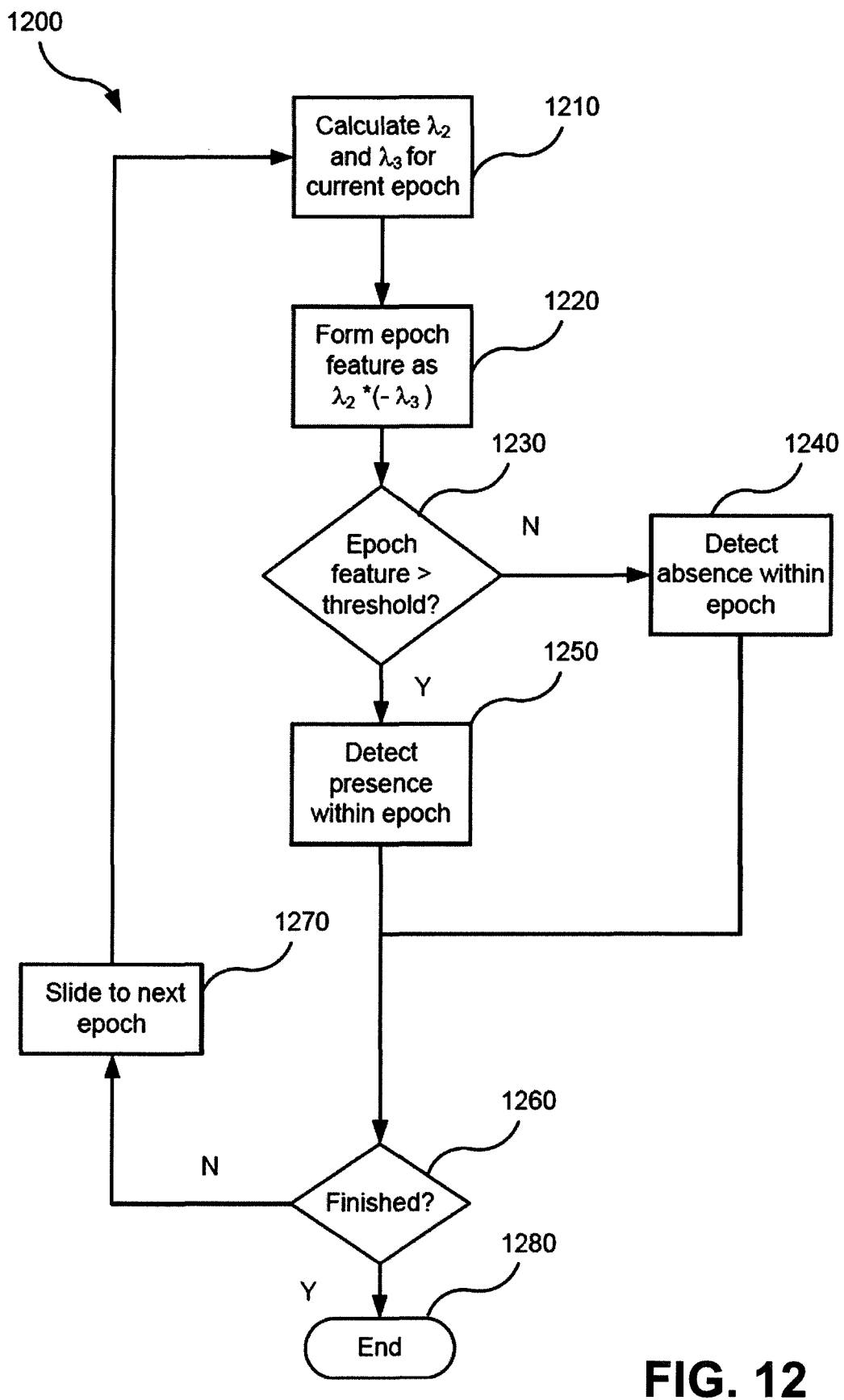
FIG. 12 is a flow chart illustrating a method that may be used to implement the presence/absence detection step of the method of FIG. 9.

FIG. 12 is a flow chart illustrating a method 1200 that may be used to implement the presence/absence detection step 920 of the method 900 in accordance with one implementation of the alternative form of the present technology. The method 1200 starts at step 1210, which extracts the second-order and third-order L-moments $\lambda_2$ and $\lambda_3$ of the combined signal, within a current epoch, e.g. using Eqs. 5 and 6. In one implementation, each epoch is of duration 5 seconds. Step 1220 then forms a feature for the current epoch by multiplying $\lambda_2$ by $-\lambda_3$. Step 1230 determines whether the epoch feature exceeds a threshold, set in one implementation to 0.01. If so ("Y"), step 1250 marks the current epoch as one in which the patient was present. Otherwise ("N"), step 1240 marks the current epoch as one in which the patient was absent. After either step 1240 or step 1250, step 1260 determines whether the end of the combined signal has been reached. If so ("Y"), the method 1200 concludes at step 1280. Otherwise, step 1270 slides to the next epoch of the combined signal. In one implementation, the slide distance is equal to the epoch duration, so the epochs are non-overlapping. The method 1200 then returns to step 1210 to analyse the next epoch.

Figure 13:
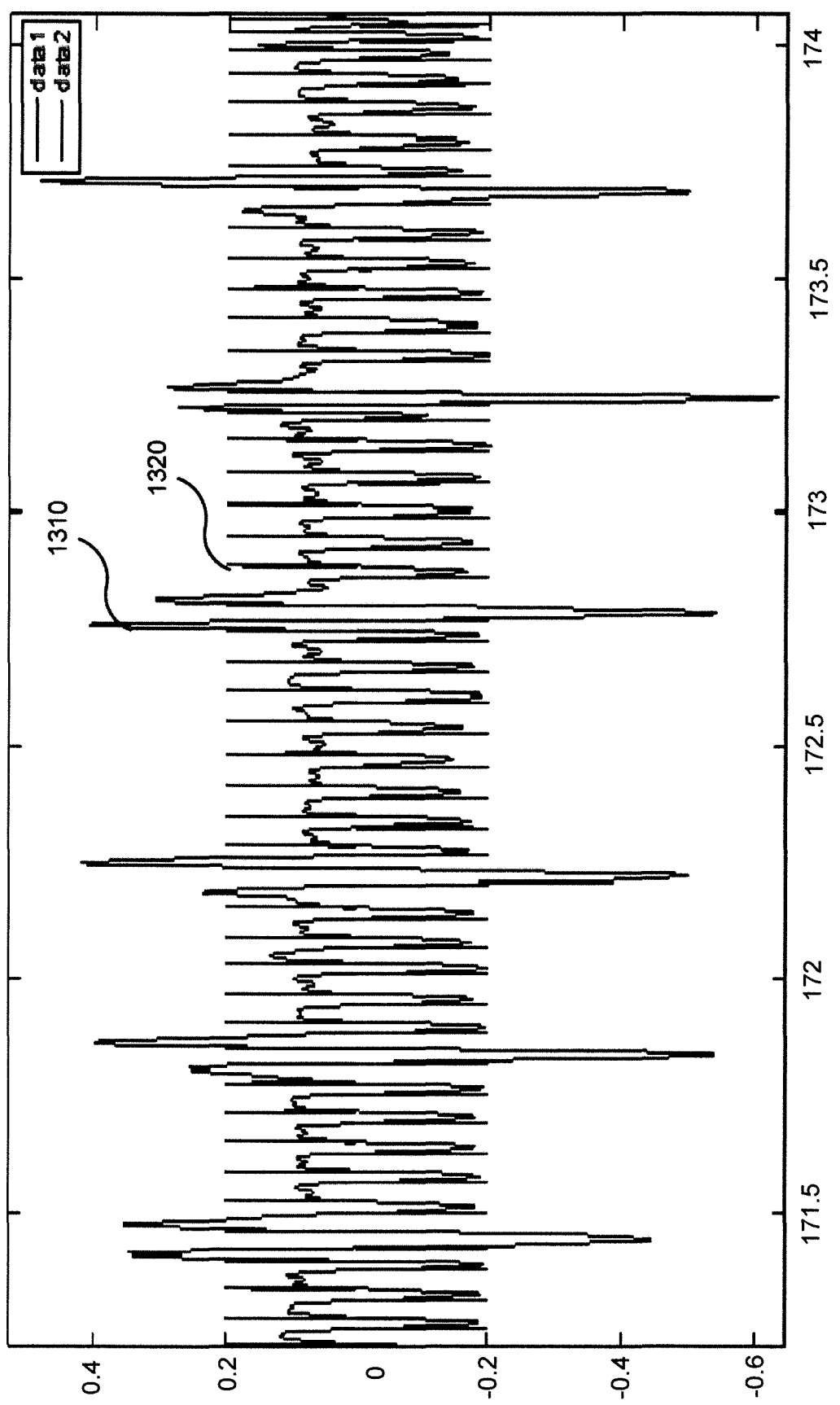
FIG. 13 is a graph illustrating the result of the method of FIG. 12 applied to an example combined signal.

At step 930 the motion signals may be partitioned into breath sections. For example, as described above, step 930 of the method 900 partitions the presence periods of the combined signal into successive breath sections where each section, or breath section, is at least associated with breathing movement representing a discrete patient breath or single respiratory cycle. One implementation of step 930 uses zero-crossing detection on the combined signal. The positive-going zero-crossing sampling instants are the locations of the start of inspiration of each breath, and the negative-going zero-crossing sampling instants are the locations of the start of expiration of each breath. Step 930 may first apply a finite impulse response (FIR) filter to the combined signal to force any zeros toward either the positive or the negative side of zero. The FIR filter is chosen so that the most recent +1 or −1 has proportionally the most influence on the state of the zero. In one implementation, the FIR filter has the form exp(−n) where n runs from 0 to the sampling frequency in Hz (one second's worth of sampling instants). FIG. 13 is a graph illustrating the result of a zero-crossing implementation of partitioning step 930 applied to a combined signal 1310. The three-valued trace 1320 has the value +1 for positive-going zero-crossings indicating the start of inspiration, −1 for negative-going zero-crossings indicating the start of expiration, and zero everywhere else.

As described above, step 940 extracts the waveform length feature from each breath section of the combined signal as returned by the partitioning step 930. Step 940 measures the cumulative changes in the combined signal from sampling instant to sampling instant over the breath section (e.g., data sample by data sample analysis of the breath section). Metaphorically, extracting the waveform length is the equivalent of treating both ends of the combined signal like the ends of a jumbled string, pulling on them until it forms a straight line, then measuring the straight-line distance. For each breath, waveform length (WL) may be computed as $$WL = \sum_{k=2}^{N} |x_k - x_{k-1}| \quad \text{(Eq. 7)}$$

where $x_k$ are the samples of the combined signal and N is the number of samples in the breath section. Waveform length effectively encapsulates the amplitude, frequency, and duration of the combined signal in one formula. This feature provides excellent discriminatory power for a classifier to distinguish normal breaths from those affected by limb movements (LMs). One reason for selecting the waveform length feature for the specific purpose of detecting LMs in step 950 is that once an LM is initiated the effect of the LM usually shows on the motion signals as an amplified peak which has a sudden jump in amplitude in comparison to previous peaks as per the example in FIG. 14. Thus, as the waveform length feature produces an amplified output for such a different peak, this feature lends itself to the specific task of LM detection.

Figure 14:
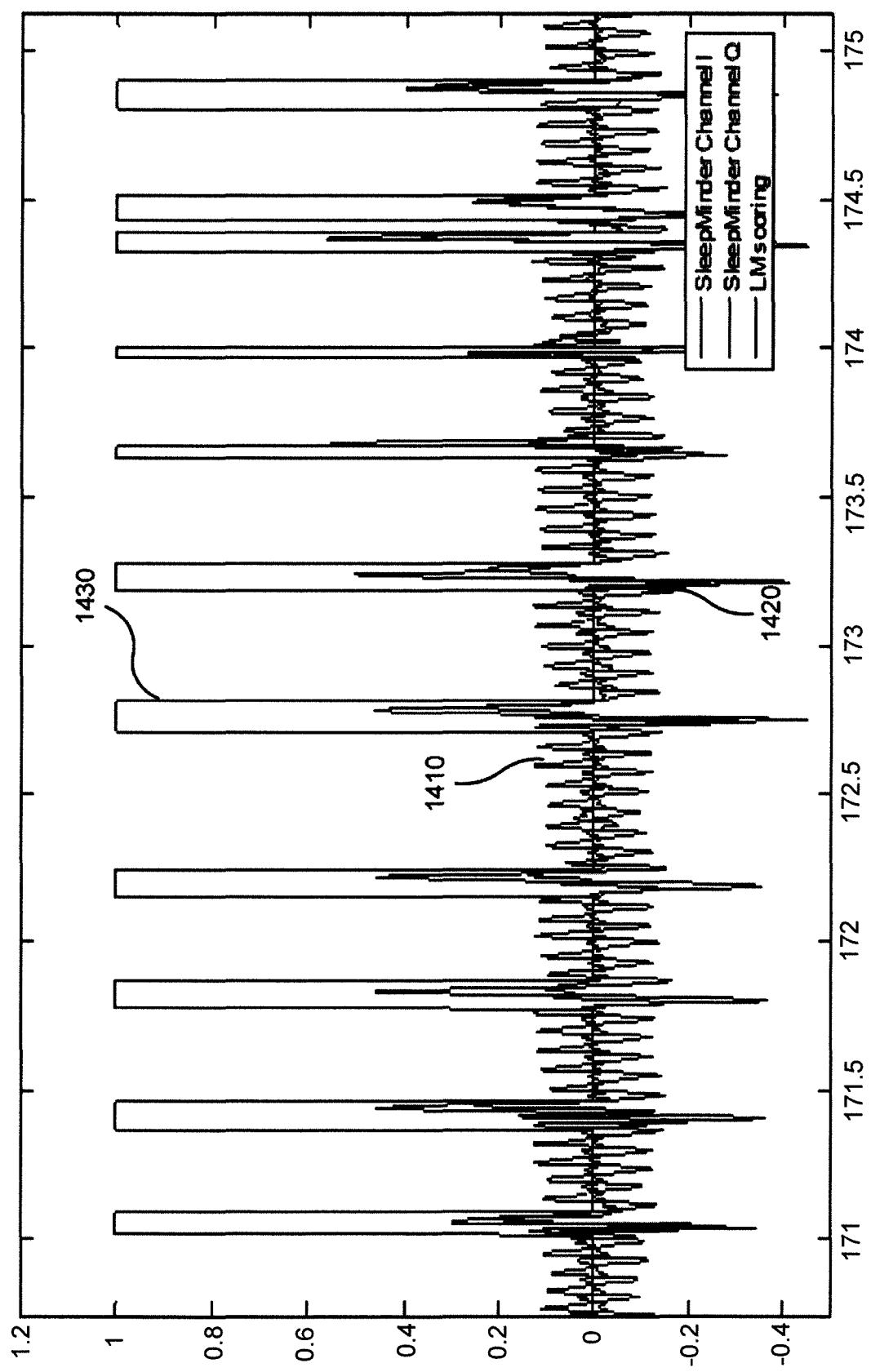
FIG. 14 is a graph illustrating the result of applying a classifier to the waveform length feature extracted from a combined signal obtained from example I and Q motion signals.

FIG. 14 is a graph illustrating the result of applying a classifier to the waveform length feature extracted from a combined signal obtained from example I and Q motion signals 1410 and 1420. The binary trace 1430 is high for breaths classified in step 950 as containing an LM based on the waveform length feature. These generally coincide with abnormally high excursions in the I or Q motion signal.

OTHER REMARKS

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. For example, whilst the disclosure has described the detection of movements such as leg movements, the same principle is applicable to other motions, such as user moving between a lying and a sitting position in bed (and vice versa), reaching for a specific target (a table lamp, or a respiratory apparatus) etc.

It will further be understood that any reference herein to subject matter known in the field does not, unless the contrary indication appears, constitute an admission that such subject matter is commonly known by those skilled in the art to which the present technology relates.

The invention claimed is:

1. A radio frequency motion sensing apparatus for detection of a sleep disorder of a patient comprising limb movement, the apparatus comprising:
   a mixer configured to produce motion signals by mixing first radio frequency signals that are transmitted by the apparatus towards the patient with second radio frequency signals that comprise the transmitted first radio frequency signals reflected off of the patient and received by the apparatus; and
   one or more processors configured to:
   receive as input, data representing the produced motion signals;
   partition the data of the motion signals into breath sections, wherein each breath section is associated with a single respiratory cycle, wherein the partitioning includes detecting zero-crossings of the motion signals and applying a filter to the motion signals to locate starts of inspiration and expiration of respiratory cycles;
   extract a waveform length feature from samples of the motion signals of each of the breath sections;
   classify, in a classifier, each of the breath sections of the motion signals as containing a limb movement associated with the patient or not containing a limb movement associated with the patient based on an amplitude output produced with the extracted breath section waveform length feature, the amplitude output being an amplified peak having an increase in amplitude in comparison to previous peaks, wherein a presence or absence of the amplified peak respectively distinguishes a breath affected by limb movement from a breath not affected by limb movement;
   determine, based on the classified breath sections, a likelihood of the patient having the sleep disorder, wherein the determined likelihood is used to determine a severity of the sleep disorder of the patient so that an appropriate treatment of the patient can be initiated; and
   operate a treatment apparatus, wherein the treatment apparatus comprises a controller configured to adjust or maintain a provided pressure treatment in response to detected motion, the classifying, or the determined likelihood.

2. The apparatus of claim 1 further comprising a filter configured to perform filtering of the motion signals.

3. The apparatus of claim 1 wherein a processor of the one or more processors is configured to measure a phase difference between the second radio frequency signals and the first radio frequency signals.

4. The apparatus of claim 1 wherein the motion signals comprise in-phase and quadrature motion signals.

5. The apparatus of claim 1 wherein the first radio frequency signals comprise pulsed radio frequency oscillating signals.

6. The apparatus of claim 4 wherein the processor is configured to determine a result by comparing portions of the in-phase and quadrature motion signals to a noise threshold.

7. The apparatus of claim 6 wherein the processor is configured to update an action counter based on the result.

8. The apparatus of claim 7 wherein the processor is configured to increase the action counter when a portion of the motion signals is greater than the noise threshold.

9. The apparatus of claim 7 wherein the processor is configured to decrease the action counter when a portion of the motion signals is less than the noise threshold.

10. The apparatus of claim 1 wherein a processor of the one or more processors is configured to compare the motion signals to a noise threshold.

11. The apparatus of claim 6 wherein the noise threshold is defined as a frequency range in-band power of noise of the motion signals.

12. The apparatus of claim 11 wherein the frequency range comprises a range of four Hertz to eight Hertz.

13. The apparatus of claim 6 wherein the processor is configured to update the noise threshold based on determined average noise of the motion signals.

14. The apparatus of claim 1 wherein a processor of the one or more processors is configured to detect a movement incident based on a comparison of a determined action count and a count threshold.

15. The apparatus of claim 14 wherein the processor is configured to determine a velocity of the movement incident.

16. The apparatus of claim 15 wherein the processor is configured to determine the velocity based on a difference between a phase of the motion signals at adjacent samples.

17. The apparatus of claim 16 wherein the processor is configured to determine displacement based on the determined velocity.

18. The apparatus of claim 17 wherein the processor is configured to determine mean displacement from absolute values of determined velocities.

19. The apparatus of claim 14 wherein the processor is configured to characterize the movement incident based on a determined mean displacement of the movement incident.

20. The apparatus of claim 19 wherein the processor is configured to generate a mapped activity value from the determined mean displacement.

21. The apparatus of claim 1 wherein a processor of the one or more processors is configured to calculate and assess a plurality of features derived from the motion signals.

22. The apparatus of claim 21 wherein the plurality of features comprise at least one of the following:
a duration of a movement incident; a total activity of a detected movement incident; a mapped total activity of a detected movement incident; a cross-correlation of in-phase and quadrature motion signals of the motion signals during a detected movement incident; and a mean of a four quadrant inverse tangent function of real parts of in-phase and quadrature motion signals of the motion signals during a detected movement incident.

23. The apparatus of claim 21 wherein the assessing comprises logistic regression.

24. The apparatus of claim 1, wherein a processor of the one or more processors is further configured to pre-process the motion signals before partitioning the motion signals to de-trend and smooth the motion signals.

25. The apparatus of claim 1, wherein a processor of the one or more processors is further configured to combine the motion signals to form a combined signal.

26. The apparatus of claim 25, wherein the processor is configured to perform principal component analysis to combine the motion signals.

27. The apparatus of claim 25, wherein the processor is further configured to discard periods of absence from the combined signal before partitioning the motion signals.

28. The apparatus of claim 27, wherein the filter for the partitioning of the motion signals comprises a finite impulse response filter.

29. The apparatus of claim 1, wherein a processor of the one or more processors is configured to score the breath sections classified as containing limb movements as part of a periodic limb movement (PLM) series according to scoring criteria.

30. The apparatus of claim 29, wherein the processor is configured to count limb movements forming part of a PLM series from a night's sleep session.

31. The apparatus of claim 1, wherein the sleep disorder occurs while the patient is sleeping, and the sleep disorder is periodic limb movement (PLM).

32. The apparatus of claim 1, wherein a positive-going zero-crossing is a location of a start of inspiration of a respiratory cycle, and a negative-going zero-crossing is a location of a start of expiration of a respiratory cycle.

33. A method for detecting a sleep disorder of a patient that includes limb movement, the method comprising:
producing, by a mixer, motion signals by mixing first radio frequency signals that are transmitted towards the patient with second radio frequency signals that comprise the transmitted first radio signals reflected off of the patient;
receive as input in a processor, data representing the produced motion signals;
partitioning, by the processor, the motion signals into breath sections, wherein each breath section is associated with a single respiratory cycle, wherein the partitioning includes detecting zero-crossings of the motion signals and applying a filter to the motion signals to locate starts of inspiration and expiration of respiratory cycles;
extracting a waveform length feature from samples of the motion signals of each of the breath sections;
classifying, in a classifier of the processor, each of the breath sections of the motion signals as containing a limb movement associated with the patient or not containing a limb movement associated with the patient based on an amplitude output produced with the extracted breath section waveform length feature, the amplitude output being an amplified peak having an increase in amplitude in comparison to previous peaks, wherein a presence or absence of the amplified peak respectively distinguishes a breath affected by limb movement from a breath not affected by limb movement;
determining, by the processor based on the classified breath sections, a likelihood of the patient having sleep disorder, wherein the determined likelihood is used to determine a severity of the sleep disorder of the patient so that an appropriate treatment of the patient can be initiated; and operate a treatment apparatus, wherein the treatment apparatus comprises a controller configured to adjust or maintain a provided pressure treatment in response to detected motion, the classifying, or the determined likelihood.

34. The method of claim 33 further comprising filtering, by a filter, the motion signals.

35. The method of claim 33 further comprising measuring, by the processor, a phase difference between the second radio frequency signals and the first radio frequency signals.

36. The method of claim 33 wherein the motion signals comprise in-phase and quadrature motion signals.

37. The method of claim 33 wherein the first radio frequency signals comprise pulsed radio frequency oscillating signals.

38. The method of claim 33 wherein the first radio frequency signals comprise pulsed radio frequency oscillating signals.

39. The method of claim 38 wherein the noise threshold is defined as a frequency range in-band power of noise of the motion signals.

40. The method of claim 39 wherein the frequency range comprises a range of four Hertz to eight Hertz.

41. The method of claim 38 further comprising adjusting the noise threshold based on determined average noise of the motion signals.

42. The method of claim 36 further comprising determining a result by comparing portions of the in-phase and quadrature motion signals to a noise threshold.

43. The method of claim 42 further comprising updating an action counter based on the result.

44. The method of claim 43 further comprising increasing the action counter when a portion of the motion signals is greater than the noise threshold.

45. The method of claim 43 further comprising decreasing the action counter when a portion of the motion signals is less than the noise threshold.

46. The method of claim 33 further comprising detecting a movement incident based on a comparison of a determined action count and a count threshold.

47. The method of claim 46 further comprising determining a velocity of the movement incident.

48. The method of claim 47 wherein the velocity is determined based on a difference between a phase of the motion signals at adjacent samples.

49. The method of claim 48 further comprising determining displacement based on the determined velocity.

50. The method of claim 49 further comprising determining mean displacement from absolute values of determined velocities.

51. The method of claim 46 further comprising characterizing the movement incident based on a determined mean displacement.

52. The method of claim 51 further comprising comparing the determined mean displacement to a threshold and generating a mapped activity value from the mean displacement.

53. The method of claim 33 further comprising calculating and assessing a plurality of features derived from the motion signals.

54. The method of claim 53 wherein the plurality of features comprise at least one of the following:
a duration of a movement incident; a total activity count of a detected movement incident; a mapped total activity of a detected movement incident; a cross-correlation of in-phase and quadrature motion signals of the motion signals during a detected movement incident; and a mean of a four quadrant inverse tangent function of real parts of in-phase and quadrature motion signals of the motion signals during a detected movement incident.

55. The method of claim 53 wherein the assessing comprises logistic regression.

56. The method of claim 33, further comprising pre-processing the motion signals before partitioning the motion signals to de-trend and smooth the motion signals.

57. The method of claim 33, further comprising combining the motion signals to form a combined signal.

58. The method of claim 57, wherein the combining the motion signals comprises principal component analysis.

59. The method of claim 57, further comprising discarding periods of absence from the combined signal before the partitioning the motion signals.

60. The method of claim 57, wherein the filter for the partitioning of the motion signals comprises a finite impulse response filter.

61. The method of claim 33, further comprising scoring the breath sections classified as containing limb movements as part of a periodic limb movement (PLM) series according to scoring criteria.

62. The method of claim 61, further comprising counting limb movements forming part of a PLM series from a night's sleep session.

63. The method of claim 33, wherein the sleep disorder occurs while the patient is sleeping, and the sleep disorder is periodic limb movement (PLM).

64. The method of claim 33, wherein a positive-going zero-crossing is a location of a start of inspiration of a respiratory cycle, and a negative-going zero-crossing is a location of a start of expiration of a respiratory cycle.

* * * * *